United States Patent
Gao et al.

(10) Patent No.: US 9,915,625 B2
(45) Date of Patent: Mar. 13, 2018

(54) OPTICAL DIE TO DATABASE INSPECTION

(71) Applicant: KLA-Tencor Corporation, Milpitas, CA (US)

(72) Inventors: Lisheng Gao, Morgan Hill, CA (US); Tao Luo, Fremont, CA (US); Keith Wells, Santa Cruz, CA (US); Xiaochun Li, San Jose, CA (US)

(73) Assignee: KLA-Tencor Corp., Milpitas, CA (US)

( * ) Notice: Subject to any disclaimer, the term of this patent is extended or adjusted under 35 U.S.C. 154(b) by 0 days.

(21) Appl. No.: 15/391,753

(22) Filed: Dec. 27, 2016

(65) Prior Publication Data

US 2017/0191948 A1 Jul. 6, 2017

Related U.S. Application Data

(60) Provisional application No. 62/274,724, filed on Jan. 4, 2016.

(51) Int. Cl.
  *G01N 21/95* (2006.01)
  *G01N 21/956* (2006.01)
  *G06T 7/00* (2017.01)

(52) U.S. Cl.
  CPC ... *G01N 21/95607* (2013.01); *G01N 21/9501* (2013.01); *G06T 7/001* (2013.01); *G01N 2201/12* (2013.01); *G06T 2207/20084* (2013.01); *G06T 2207/30148* (2013.01)

(58) Field of Classification Search
  USPC ................ 382/144, 145, 147, 149
  See application file for complete search history.

(56) References Cited

U.S. PATENT DOCUMENTS

| | | | | |
|---|---|---|---|---|
| 6,470,489 | B1 * | 10/2002 | Chang | G03F 1/36 430/5 |
| 6,902,855 | B2 | 6/2005 | Peterson et al. | |
| 6,966,047 | B1 * | 11/2005 | Glasser | G01N 21/95607 382/144 |
| 7,331,033 | B2 * | 2/2008 | Feldman | G03F 1/84 716/51 |

(Continued)

OTHER PUBLICATIONS

International Search Report for PCT/US2016/069172 dated Apr. 17, 2017.

(Continued)

*Primary Examiner* — Ishrat I Sherali
(74) *Attorney, Agent, or Firm* — Ann Marie Mewherter

(57) ABSTRACT

Methods and systems for detecting defects on a wafer are provided. One system includes one or more computer subsystems configured for generating a rendered image based on information for a design printed on the wafer. The rendered image is a simulation of an image generated by an optical inspection subsystem for the design printed on the wafer. Generating the rendered image includes one or more steps, and the computer subsystem(s) are configured for performing at least one of the one or more steps by executing a generative model. The computer subsystem(s)) are also configured for comparing the rendered image to an optical image of the wafer generated by the optical inspection subsystem. The design is printed on the wafer using a reticle. In addition, the computer subsystem(s) are configured for detecting defects on the wafer based on results of the comparing.

35 Claims, 9 Drawing Sheets

(56) References Cited

U.S. PATENT DOCUMENTS

| | | | |
|---|---|---|---|
| 7,383,530 B2* | 6/2008 | Wang | G03F 1/36 430/30 |
| 7,418,124 B2 | 8/2008 | Peterson et al. | |
| 7,564,545 B2* | 7/2009 | Stokowski | G03F 7/705 356/237.5 |
| 7,570,796 B2 | 8/2009 | Zafar et al. | |
| 7,676,077 B2 | 3/2010 | Kulkarni et al. | |
| 7,769,225 B2 | 8/2010 | Kekare et al. | |
| 8,041,106 B2 | 10/2011 | Pak et al. | |
| 8,126,255 B2 | 2/2012 | Bhaskar et al. | |
| 8,213,704 B2 | 7/2012 | Peterson et al. | |
| 9,222,895 B2 | 12/2015 | Duffy et al. | |
| 9,671,685 B2* | 6/2017 | Lin | G03F 1/72 |
| 2007/0035728 A1 | 2/2007 | Kekare et al. | |
| 2008/0167829 A1 | 7/2008 | Park et al. | |
| 2008/0170774 A1* | 7/2008 | Xiong | G01N 21/95607 382/144 |
| 2012/0307218 A1 | 12/2012 | Kamo | |
| 2015/0324963 A1 | 11/2015 | Sezginer et al. | |
| 2015/0356233 A1 | 12/2015 | Fouquet et al. | |
| 2016/0290934 A1* | 10/2016 | Wells | G01N 21/9501 |
| 2017/0018064 A1* | 1/2017 | Seidel | G06T 7/001 |
| 2017/0140524 A1 | 5/2017 | Bhaskar et al. | |
| 2017/0148226 A1 | 5/2017 | Zhang et al. | |
| 2017/0191948 A1* | 7/2017 | Gao | G01N 21/95607 |

OTHER PUBLICATIONS

Written Opinion for PCT/US2016/069172 dated Apr. 17, 2017.

U.S. Appl. No. 15/088,081, filed Mar. 31, 2016 by Wells et al. (submitted as U.S. Patent Application Publication No. 2016/0290934 published Oct. 6, 2016 by Wells et al.).

U.S. Appl. No. 15/176,139, filed Jun. 7, 2016 by Zhang et al. (submitted as U.S. Patent Application Publication No. 2017/0148226 published May 25, 2017 by Zhang et al.).

U.S. Appl. No. 15/353,210, filed Nov. 16, 2016 by Bhaskar et al. (submitted as U.S. Patent Application Publication No. 2017/0140524 published May 18, 2017 by Bhaskar et al.).

Deng, "A tutorial survey of architectures, algorithms, and applications for deep learning," APSIPA, Transactions on Signal and Information Processing, vol. 3, 2014, 29 pages.

Kingma et al., "Auto-Encoding Variational Bayes," arXiv:1312.6114v10, May 1, 2014, 14 pages.

Kulkarni et al., "Deep Convolutional Inverse Graphics Network," arXiv:1503.03167v3, Jun. 22, 2015, 10 pages.

Ranzato, "Supervised Deep Learning," CVPR Jun. 23, 2014, 126 pages.

Taylor et al., "CVPR 2014 Tutorial Deep Learning for Computer Vision," Jun. 23, 2014, 46 pages.

* cited by examiner

OPTICAL DIE TO DATABASE INSPECTION

BACKGROUND OF THE INVENTION

1. Field of the Invention

This invention generally relates to methods and systems for detecting defects on a wafer by optical die to database inspection.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, hut are not limited to, chemical-mechanical polishing (CMP), etch, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as ICs. However, as the dimensions of semiconductor devices decrease, inspection becomes even more important to the successful manufacture of semiconductor devices.

Many reticle inspection methods detect defects on reticles using die-to-database type comparisons. Such inspection typically involves acquiring a microscope image of a reticle. From a database that describes the intended pattern on the reticle, an image that the inspection microscope is expected to observe of that reticle may be calculated or simulated. The acquired optical image may then be compared to the calculated or simulated image to detect defects on the reticle. Such reticle inspection methods have proven useful for a number of uses. However, such reticle inspection methods are not capable of finding process-induced defects (i.e., defects that would be printed on a wafer due to the interaction between the reticle and the process of printing the reticle on the wafer).

Some reticle inspections are performed using wafers that have been printed with the reticles. In this manner, defects that are detected on the wafer can be used to determine if there are defects on the reticle that was used to print the wafer. Some such inspections are performed on optical platforms by comparing an inspected image frame to a reference frame, where the reference frame is a sample of the image generated from the wafer. Examples for reference image frames are: images from adjacent dies, images from a standard reference die on the same wafer or a different wafer, and images from the adjacent cells (in an array structure).

Currently, die to database inspection performed for wafers exists only on a scanning electron microscope (SEM) inspection platform. However, due to the throughput constraints (e.g., due to the physics of electron beam tools), only a substantially small number of locations (i.e., not the entire wafer and not entire dies on the wafer) can be checked. In addition, inspection performed by electron beam inspection of wafers is too slow to qualify every reticle for which qualification is needed. Furthermore, with the advent of multiple patterning step lithography processes, and as a result needing multiple reticle qualifications for a single lithography process, the number of reticles for which qualification must be performed should grow substantially.

The currently available optical inspection methodologies that involve comparing wafer images to a reference wafer image to detect defects on a wafer cannot serve some of the use cases for which such inspection is performed. For example, such currently used optical inspections cannot detect repeater defects within dies printed with a single die reticle. One example of such a use case is for extreme ultraviolet (EUV) mask qualification. In particular, due to the lack of a pellicle, particles on the mask when printed on the wafer become repeater defects on the wafer. Therefore, such defects will cancel each other out in die-to-die comparisons and not be detected. In addition, such currently used optical inspections cannot be used for design intent checks. For example, a reference image generated from part of a wafer contains the process variation. Therefore, comparison of such a reference image with a different wafer image will cancel out the process variation in both images rendering the process variation undetectable. Furthermore, before the process becomes mature, it is difficult to find a "golden" reference die. For example, a user may have no idea which die or dies can be used as a "golden" reference die for comparison with other dies on a wafer.

Accordingly, it would be advantageous to develop systems and/or methods for detecting defects on a wafer that do not have one or more of the disadvantages described above.

SUMMARY OF THE INVENTION

The following description of various embodiments is not to be construed in any way as limiting the subject matter of the appended claims.

One embodiment relates to a system configured to detect defects on a wafer. The system includes an optical inspection subsystem that includes at least a light source and a detector. The light source is configured to generate light that is directed to a wafer. The detector is configured to detect light from the wafer and to generate output responsive to the detected light. The system also includes one or more computer subsystems configured for generating a rendered image based on information for a design printed on the wafer. The rendered image is a simulation of an image generated by the optical inspection subsystem for the design printed on the wafer. Generating the rendered image includes one or more steps. The one or more computer subsystems are configured for performing at least one of the one or more steps by executing a generative model. The computer subsystem(s) are also configured for comparing the rendered image to an optical image of the wafer generated by the optical inspection subsystem. The design is printed on the wafer using a reticle. The computer subsystem(s) are further configured for detecting defects on the wafer based on results of the comparing. The system may be further configured as described herein.

Another embodiment relates to a computer-implemented method for detecting defects on a wafer. The method includes steps for each of the functions of the one or more computer subsystems described above. The steps of the method are performed by one or more computer systems. The method may be performed as described further herein. In addition, the method may include any other step(s) of any other method(s) described herein. Furthermore, the method may be performed by any of the systems described herein.

An additional embodiment relates to a non-transitory computer-readable medium storing program instructions executable on a computer system for performing a computer-implemented method for detecting defects on a wafer. The computer-implemented method includes the steps of the method described above. The computer-readable medium may be further configured as described herein. The steps of the computer-implemented method may be performed as described further herein. In addition, the computer-implemented method for which the program instructions are executable may include any other step(s) of any other method(s) described herein.

BRIEF DESCRIPTION OF THE DRAWINGS

Other objects and advantages of the invention will become apparent upon reading the following detailed description and upon reference to the accompanying drawings in which.

Figure 1:
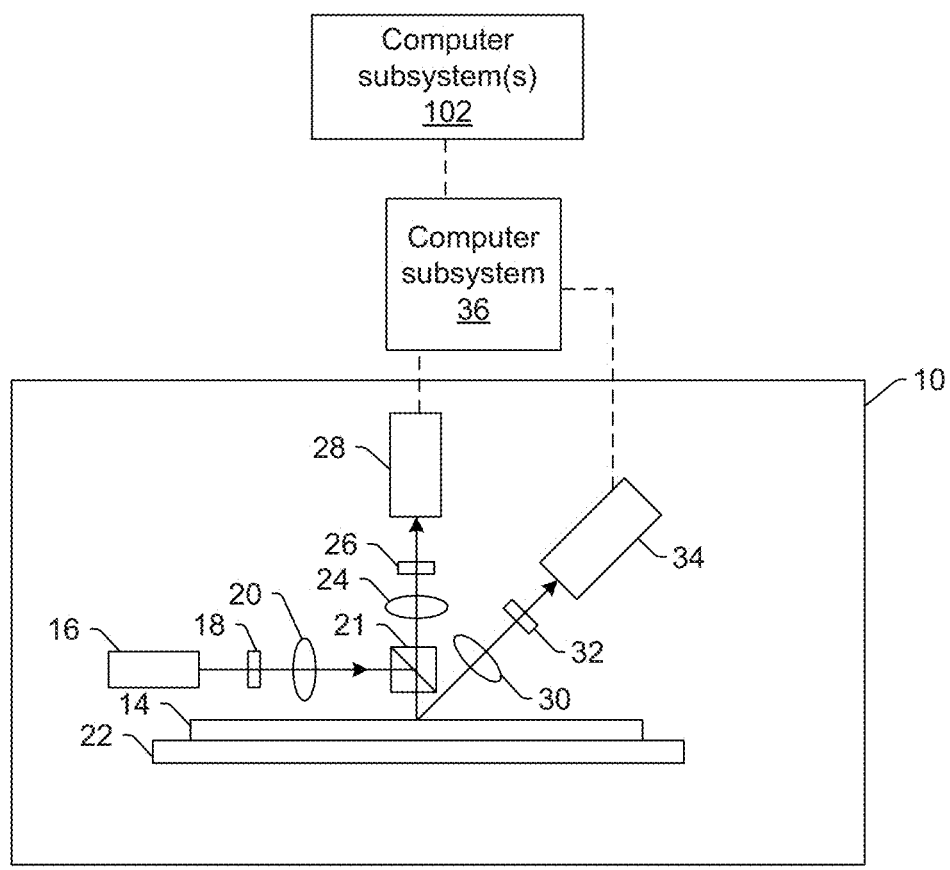
FIG. 1 is a schematic diagram illustrating a side view of an embodiment of a system configured as described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The terms "design" and "design data" as used herein generally refer to the physical design (layout) of an IC and data derived from the physical design through complex simulation or simple geometric and Boolean operations. The design may include any other design data or design data proxies described in commonly owned U.S. Pat. No. 7,570,796 issued on Aug. 4, 2009 to Zafar et al. and U.S. Pat. No. 7,676,077 issued on Mar. 9, 2010 to Kulkarni et al., both of which are incorporated by reference as if fully set forth herein. In addition, the design data can be standard cell library data, integrated layout data, design data for one or more layers, derivatives of the design data, and full or partial chip design data.

In general, however, the design information or data cannot be generated by is imaging a wafer with a wafer inspection system. For example, the design patterns formed on the wafer may not accurately represent the design for the wafer and the wafer inspection system may not be capable of generating images of the design patterns formed on the wafer with sufficient resolution such that, the images could be used to determine information about the design for the wafer. Therefore, in general, the design information or design data cannot be generated using a physical wafer. In addition, the "design" and. "design data" described herein refers to information and data that is generated by a semiconductor device designer in a design process and is therefore available for use in the embodiments described herein well in advance of printing of the design on any physical wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals. Unless otherwise noted herein, any of the elements described and shown may include any suitable commercially available elements.

One embodiment relates to a system configured to detect defects on a wafer. In general, the embodiments described herein are configured for optical die-to-database (DB) inspection of wafers performed using a deep learning (DL) technique. In other words, the embodiments described herein are generally configured for comparing an optical image of a wafer printed with a reticle to a rendered image generated from a DB using one or more DL, engines to detect defects on the wafer.

The wafer may include any wafer known in the art. The design is printed on the wafer using a reticle. The design may be printed on the wafer using the reticle in any suitable manner known in the art (e.g., by depositing one or more materials on a wafer and performing a lithography process on the wafer to transfer the design from the reticle to the wafer). The wafer may also be a short loop wafer, meaning a wafer on which not all process steps required to ultimately form a functioning device have been performed. In other words, the wafer may or may not be a full loop wafer. For example, the wafer may be a wafer on which only the process steps described above (e.g., deposition, lithography, and possibly etch) have been performed. As such, the wafer may not include one or more layers (patterned and/or unpatterned) formed under the layer of the wafer being inspected. In this manner, the process steps that are performed on the wafer prior to the inspection described herein may include only those required to transfer a design for the wafer from a reticle to the wafer. The reticle may include any reticle known in the art such as reticles configured for use with extreme ultraviolet (EUV) light or another suitable type of light.

One embodiment of such a system is shown in FIG. 1. The system includes an optical inspection subsystem that includes at least a light source and a detector. The light source is configured to generate light that is directed to a wafer. The detector is configured to detect light from the wafer and to generate output responsive to the detected light.

In the embodiment of the system shown in FIG. 1, optical inspection subsystem 10 includes an illumination subsystem configured to direct light to wafer 14. The illumination subsystem includes at least one light source. For example, as shown in FIG. 1, the illumination subsystem includes light source 16. In one embodiment, the illumination subsystem is configured to direct the light to the wafer at one or more angles of incidence, which may include one or more oblique angles and/or one or more normal angles. For example, as shown in FIG. 1, light from light source 16 is directed through optical element 18 and then lens 20 to beam splitter 21, which directs the light, to wafer 14 at a normal angle of incidence. The angle of incidence may include any suitable angle of incidence, which may vary depending on, for instance, characteristics of the wafer and the defects to be detected on the wafer.

The illumination subsystem may be configured to direct the light to the wafer at different angles of incidence at different times. For example, the inspection subsystem may be configured to alter one or more characteristics of one or more elements of the illumination subsystem such that the light can be directed to the wafer at an angle of incidence that is different than that shown in FIG. 1. In one such example, the inspection subsystem may be configured to move light source 16, optical element 18, and lens 20 such that the light is directed to the wafer at a different angle of incidence.

In some instances, the inspection subsystem may be configured to direct light to the wafer at more than one angle of incidence at the same time. For example, the illumination subsystem may include more than one illumination channel, one of the illumination channels may include light source 16, optical element 18, and lens 20 as shown in FIG. 1 and another of the illumination channels (not shown) may include similar elements, which_ may be configured differently or the same, or may include at least a light source and possibly one or more other components such as those described further herein. If such light is directed to the wafer at the same time as the other light, one or more characteristics (e.g., wavelength, polarization, etc.) of the light directed to the wafer at different angles of incidence may be different such that light resulting from illumination of the wafer at the different angles of incidence can be discriminated from each other at the detector(s), In another instance, the illumination subsystem may include only one light source (e.g., source 16 shown in FIG. 1) and light from the light source may be separated into different optical paths (e.g., based on wavelength, polarization, etc.) by one or more optical elements (not shown) of the illumination subsystem. Light in each of the different optical paths may then be directed to the wafer. Multiple illumination channels may be configured to direct light to the wafer at the same time or at different times (e.g., when different illumination channels are used to sequentially illuminate the wafer). In another instance, the same illumination channel may be configured to direct light to the wafer with different characteristics at different times. For example, in some instances, optical element 18 may be configured as a spectral filter and the properties of the spectral filter can be changed in a variety of different ways (e.g., by swapping out the spectral filter) such that different wavelengths of light can be directed to the wafer at different times. The illumination subsystem may have any other suitable configuration known in the art for directing light having different or the same characteristics to the wafer at different or the same angles of incidence sequentially or simultaneously.

In one embodiment, light source 16 may include a broadband plasma (BBP) light source. In this manner, the light generated by the light source and directed to the wafer may include broadband light. However, the light source may include any other suitable light source such as a laser. The laser may include any suitable laser known in the art and may be configured to generate light at any suitable wavelength or wavelengths known in the art. In addition, the laser may be configured to generate light that is monochromatic or nearly-monochromatic. In this manner, the laser may be a narrowband laser. The light source may also include a polychromatic light source that generates light at multiple discrete wavelengths or wavebands.

Light from optical element 18 may be focused to beam splitter 21 by lens 20. Although lens 20 is shown in FIG. 1 as a single refractive optical element, it is to be understood that, in practice, lens 20 may include a number of refractive and/or reflective optical elements that in combination focus the light from the optical element, to the wafer. The illumination subsystem shown in FIG. 1 and described herein may include any other suitable optical elements (not shown). Examples of such optical elements include, but are not limited to, polarizing component(s), spectral filter(s), spatial filter(s), reflective optical element(s), apodizer(s), beam splitter(s), aperture(s), and the like, which may include any such suitable optical elements known in the art. In addition, the system may be configured to alter one or more of the elements of the illumination subsystem based on the type of illumination to be used for inspection.

The inspection subsystem may also include a scanning subsystem configured to cause the light to be scanned over the wafer. For example, the inspection subsystem may include stage 22 on which wafer 14 is disposed during inspection. The scanning subsystem may include any suitable mechanical and/or robotic assembly (that includes stage 22) that can be configured to move the wafer such that the light can be scanned over the wafer. In addition, or alternatively, the inspection subsystem may he configured such that one or more optical elements of the inspection subsystem perform some scanning of the light over the wafer. The light may be scanned over the wafer in any suitable fashion.

The inspection subsystem further includes one or more detection channels. At least one of the one or more detection channels includes a detector configured to detect light from the wafer due to illumination of the wafer by the inspection subsystem and to generate output responsive to the detected tight. For example, the inspection subsystem shown in FIG. 1 includes two detection channels, one formed by collector 24, element 26, and detector 28 and another formed by collector 30, element 32, and detector 34. As shown in FIG. 1, the two detection channels are configured to collect and detect light at different angles of collection. In some instances, one detection channel is configured to detect specularly reflected light, and the other detection channel is configured to detect light that is not specularly reflected (e.g., scattered, diffracted, etc.) from the wafer. However, two or more of the detection channels may be configured to detect the same type of light from the wafer (e.g., specularly reflected light). Although FIG. 1 shows an embodiment of the inspection subsystem that includes two detection channels, the inspection subsystem may include a different number of detection channels (e.g., only one detection channel or two or more detection channels). Although each of the collectors are shown in FIG. 1 as single refractive optical elements, it is to be understood that each of the collectors may include one or more refractive optical element(s) and/or one or more reflective optical element(s).

The one or more detection channels may include any suitable detectors known in the art. For example, the detectors may include photo-multiplier tubes (PMTs), charge coupled devices (CCDs), and time delay integration (TDI) cameras. The detectors may also include any other suitable detectors known in the art. The detectors may also include non-imaging detectors or imaging detectors. In this manner, if the detectors are non-imaging detectors, each of the detectors may be configured to detect certain characteristics of the scattered light such as intensity but may not be configured to detect such characteristics as a function of position within the imaging plane. As such, the output that is generated by each of the detectors included in each of the detection channels of the inspection subsystem may be signals or data, but not image signals or image data. In such instances, a computer subsystem such as computer subsystem 36 of the system may be configured to generate images of the wafer from the non-imaging output of the detectors. However, in other instances, the detectors may be configured as imaging detectors that are configured to generate imaging signals or image data. Therefore, the system may be configured to generate the output described herein in a number of ways.

It is noted that FIG. 1 is provided herein to generally illustrate a configuration of an inspection subsystem that may be included in the system embodiments described herein. Obviously, the inspection subsystem configuration described herein may be altered to optimize the performance of the system as is normally performed when designing a commercial inspection system. In addition, the systems described herein may be implemented using an existing inspection system (e.g., by adding functionality. described herein to an existing inspection system) such as the 28xx and 29xx series of tools that are commercially available from KLA-Tencor. For some such systems, the methods described herein may be provided as optional functionality of the system (e.g., in addition to other functionality of the system). Alternatively, the system described herein may he designed "from scratch" to provide a completely new system.

The optical inspection subsystem shown in FIG. 1 may also be configured as an optical defect review subsystem by alteration of one or more parameters of the inspection subsystem (e.g., to increase the resolution of the inspection subsystem), which may be performed in any suitable manner known in the art. In this manner, the systems described herein may be configured to perform defect review and/or classification using comparisons such as those described herein. Defect review and/or classification may otherwise be performed in any suitable manner known in the art.

Computer subsystem 36 of the system may be coupled to the detectors of the inspection subsystem in any suitable manner (e.g., via one or more transmission media, which may include "wired" and/or "wireless" transmission media) such that the computer subsystem can receive the output generated by the detectors during scanning of the wafer. Computer subsystem 36 may be configured to perform a number of functions using the output of the detectors as described herein and any other functions described further herein. This computer subsystem may he further configured as described herein.

This computer subsystem (as well as other computer subsystems described herein) may also be referred to herein as computer system(s). Each of the computer subsystem(s) or system(s) described herein may take various forms, including a personal computer system, image computer, mainframe computer system, workstation, network appliance, Internet appliance, or other device. In general, the term "computer system" may be broadly defined to encompass any device having one or more processors, which executes instructions from a memory medium. The computer subsystem(s) or system(s) may also include any suitable processor known in the art such as a parallel processor. In addition, the computer subsystem(s) or system(s) may include a computer platform with high speed processing and software, either as a standalone or a networked tool.

If the system includes more than one computer subsystem, then the different computer subsystems may be coupled to each other such that images, data, information, instructions, etc. can be sent between the computer subsystems as described further herein. For example, computer subsystem 36 may be coupled to computer subsystem(s) 102 (as shown by the dashed line in FIG. 1) by any suitable transmission media, which may include any suitable wired and/or wireless transmission media known in the art. Two or more of such computer subsystems may also be effectively coupled by a shared computer-readable storage medium (not shown).

Figure 2:
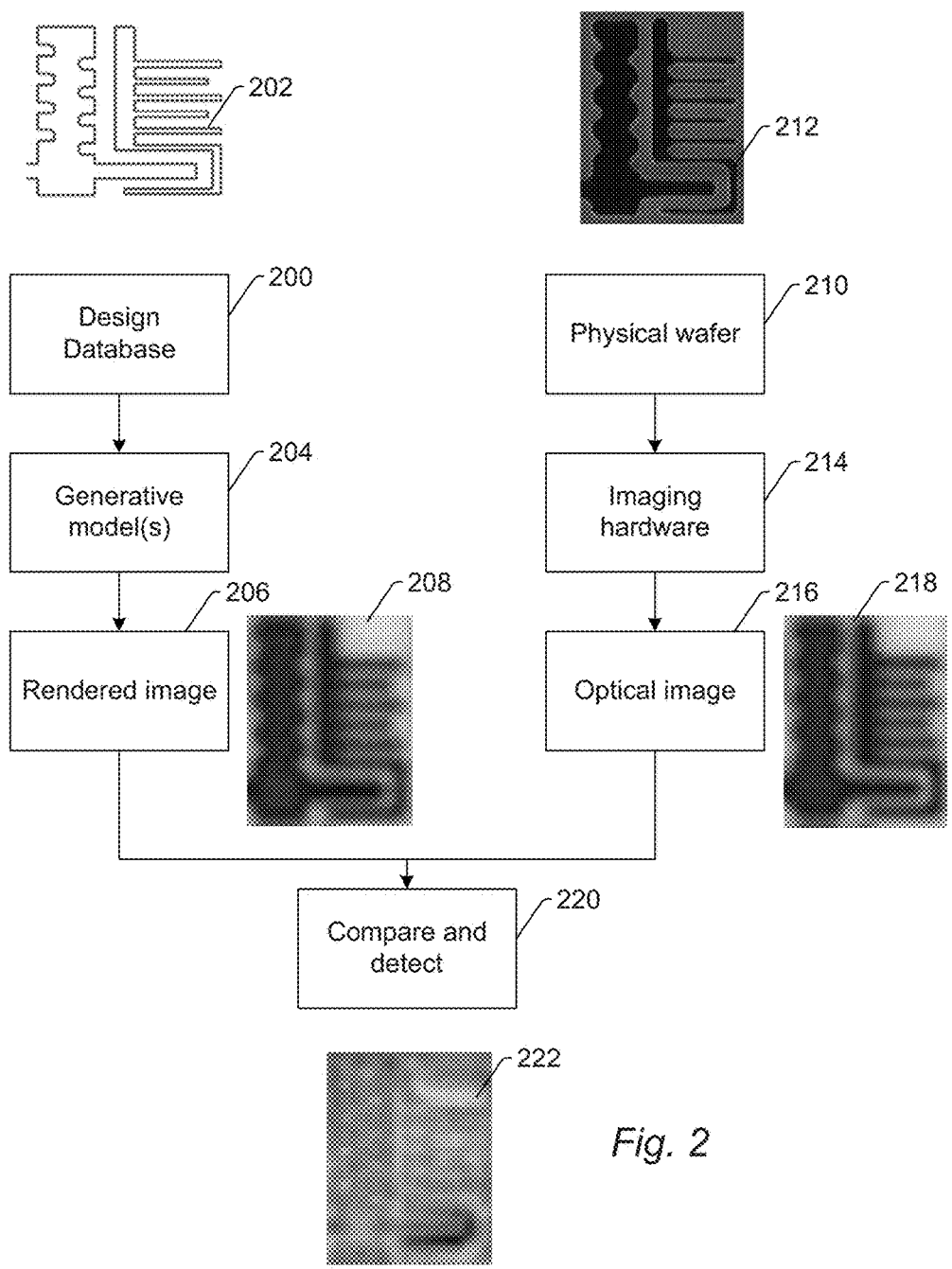
FIG. 2 is a flow chart illustrating one embodiment of steps that may be performed by one or more computer subsystems described herein.

The one or more computer subsystems described above are configured for generating a rendered image based on information for a design printed on the wafer. The rendered image is a simulation of an image generated by the optical inspection subsystem for the design printed on the wafer. Generating the rendered image includes one or more steps, and the one or more computer subsystems are configured for performing at least one of the one or more steps by executing a generative model. For example, as shown in FIG. 2, the computer subsystem(s) may be configured to acquire design database 200, which may include design polygons 202 or other design information described herein. The computer subsystem(s) may use generative model(s) 204 to generate rendered image 206 from design database 200. Each of the generative models may perform image rendering with a deep learning technique. The generative model(s) and the deep learning technique(s) may include any of those described further herein. In this manner, a deep learning approach can be applied to generate a rendered image from design. Therefore, the computer subsystem(s) may use design polygons 202 as input to generative model(s) that output rendered image 206, one of example of which is shown in FIG. 2 as rendered image 208.

In this manner, the computer subsystem(s) are configured for generating a simulated optical inspection image from design. In addition, the computer subsystem(s) are configured for generating a simulated optical image from design using one or more generative models to perform one or more steps involved in generating the simulated image. The generative modeling can be performed in a number of different manners described further herein. For example, the computer subsystem(s) may use a generative model to model from design (polygons) with estimated near field and an accurate or approximate optical system model. In another example, the computer subsystem(s) may use a generative model to model from a stack of geometry and material information to calculate or estimate the near field and to learn and use an accurate or approximate optical system model.

The computer subsystem(s) are also configured for comparing the rendered image to an optical image of the wafer generated by the optical inspection subsystem and detecting defects on the wafer based on results of the comparing. The design is printed on the wafer using a reticle. For example, as shown in FIG. 2, physical wafer 210 may be printed with the design for the wafer using the reticle. In one such example, design 212 may be printed on wafer 210. Imaging hardware 214 (i.e., an optical inspection subsystem as described herein) may then generate optical image 216 of the physical wafer. One example of such an optical image is shown in FIG. 2 as optical image 218. The computer subsystem(s) may then perform compare and detect, as shown in step 220, by comparing rendered image 206 and optical image 216 and detecting defects based on the comparison results. For example, the computer subsystem(s) may subtract rendered image 208 from optical image 218 thereby generating difference image 222. In this manner, the computer subsystem(s) may be configured for comparing the optical wafer image to a rendered image from design.

The computer subsystem(s) may then detect defects on the wafer in any suitable manner using the difference image. For example, the computer subsystem(s)) may apply one or more defect detection algorithms and/or methods to the difference image. In one such example, the computer subsystem(s) may compare signals or data in difference image 222 to a threshold. Any of the signals or data that are above the threshold may be identified as defects or potential defects, while any of the signals or data that are below the threshold may not be identified as defects or potential defects. Of course, many other defect detection algorithms and methods are known in the art, and the embodiments described herein are not limited to any one defect detection algorithm or method. In other words, the results of the comparison described herein may be input to any suitable defect detection algorithm and/or method known in the art.

In some embodiments, the one or more computer subsystems are further configured for determining if the reticle passes qualification based on the detected defects. Determining if the reticle passes qualification based on the defects detected on the wafer may be performed in any suitable manner known in the art. One advantage of the embodiments described herein is that they can perform die-to-DB inspection for EUV mask qualification. Different from normal optical masks, an EUV mask qualification system is not currently available because of the lack of actinic EUV mask inspection systems. However, the embodiments described herein may be used for reticle qualification of any type of reticle known in the art. In this manner, the printability of the reticle on wafer may be validated through the die-to-DB optical wafer inspection described herein as part of reticle qualification.

The embodiments described herein may also be configured for performing process window qualification (PWQ) such as that described in U.S. Pat. No. 6,902,855 to Peterson et al. issued on Jun. 7, 2005, U.S. Pat. No. 7,418,124 to Peterson et al. issued on Aug. 26, 2008, U.S. Pat. No. 7,769,225 to Kekare et al. issued on Aug. 3, 2010, U.S. Pat. No. 8,041,106 to Pak et al. issued on Oct. 18, 2011, and U.S. Pat. No. 8,213,704 to Peterson et al. issued on Jul. 3, 2012, which are incorporated by reference as if fully set forth herein. The embodiments described herein may include any step(s) of any method(s) described in these patents and may be further configured as described in these patents. A PWQ wafer may be printed as described in these patents.

In another embodiment, the one or more computer subsystems are configured for determining a performance of one or more process steps performed on the wafer based on the detected defects. In one such embodiment, the wafer is a short loop wafer. For example, a short loop wafer may be manufactured with only a subset of all of the layers that would be formed on the wafer to fabricate a fully functioning device. Such wafers may be used to check only specific process steps such as a lithography step and/or an etch step. The performance of the one or more process steps performed on the wafer based on the detected defects may be determined in any suitable manner. Once the performance of the one or more process steps has been determined, the one or more process steps may be altered in any suitable manner (e.g., by determining and altering one or more parameters of the one or more process steps based on the determined performance of the one or more process steps to thereby correct the performance of the one or more process steps, e.g., to bring the performance of the one or more process steps back into specification).

The die-to-DB for optical wafer inspection described herein is new technology. In particular, currently, there is no optical die-to-DB methodology available for wafer inspection. In addition, the die-to-DB for optical wafer inspection has a number of important advantages over other currently available methods for detecting defects on wafers. For example, the embodiments described herein can detect die-to-die repeater defects and variations from design. In addition, the embodiments described herein do not rely on using a standard reference die generated from a physical wafer for use as the DB to which wafer die images are compared. For example, standard reference dies can be used as proxies for detecting die-to-die repeater defects. However, oftentimes, it is not known Which die is suitable for use as a standard reference die. :Furthermore, there is no inspection technology available today to check the design intent.

Scanning electron microscope (SEM) die-to-DB inspection for wafers is currently available. SEM die-to-DB is commonly used today for several use cases such as for detection of critical dimension (CD) variation, where the sensitivity requirement can be as small as 2 nm. However, SEM die-to-DB is not fast enough to serve the needs of wafer inspection. For example, currently, due to throughput constraints (due to the physics of the SEM imaging process), only a substantially small number of locations can be checked. In contrast, the optical die-to-DB inspection described herein can inspect an entire wafer within an acceptable time period. In this manner, the optical die-to-DB inspection described herein can be performed much faster than SEM die-to-DB. In addition, the die-to-DB inspection described herein can be performed for any wafer known in the art and for qualifying any reticle known in the art. Therefore, the embodiments described herein enable users to do integration debugging of any new reticle that they may not have time to do with the current electron beam solutions. In addition, since SEM has substantially higher resolution than optical inspection tools and only images the top layer of a wafer, rendering a SEM image from design is relatively easy. For example, SEM images can look substantially similar to design except that the corners may be rounded. In addition, SEM die-to-DB inspection can have challenges in detection for nuisance issues.

In comparison, optical die-to-DB is a much more difficult problem than SEM die-to-DB due to optical limitations in resolution and required accuracy and throughput in simulation to create a practical product. Due to its technical difficulty, optical die-to-DB for wafer inspection is not currently available in the industry.

Some reticle inspection methods use a near field approximation for detecting defects on reticles. For example, the near field at the reticle plane may be approximated based on a thin film assumption and information about the optical path of the reticle inspection subsystem. This thin film assumption assumes the near field at the reticle plane is close to design (for lithography only one layer), which holds when wavelength and feature size are approximately the same. With today's design rule, the feature size is much smaller than wavelength even for reticles, where the feature size is 4× the feature size on wafers. Therefore, reticle plane near field approximations are becoming more and more challenging in reticle inspection. On wafers, it is even more challenging due to the 4× shrink of feature size.

The generative model may be a deep learning (DL) type model. In this manner, the embodiments described herein may be configured for optical die-to-DB wafer inspection with deep learning technique(s).

Figure 2A:
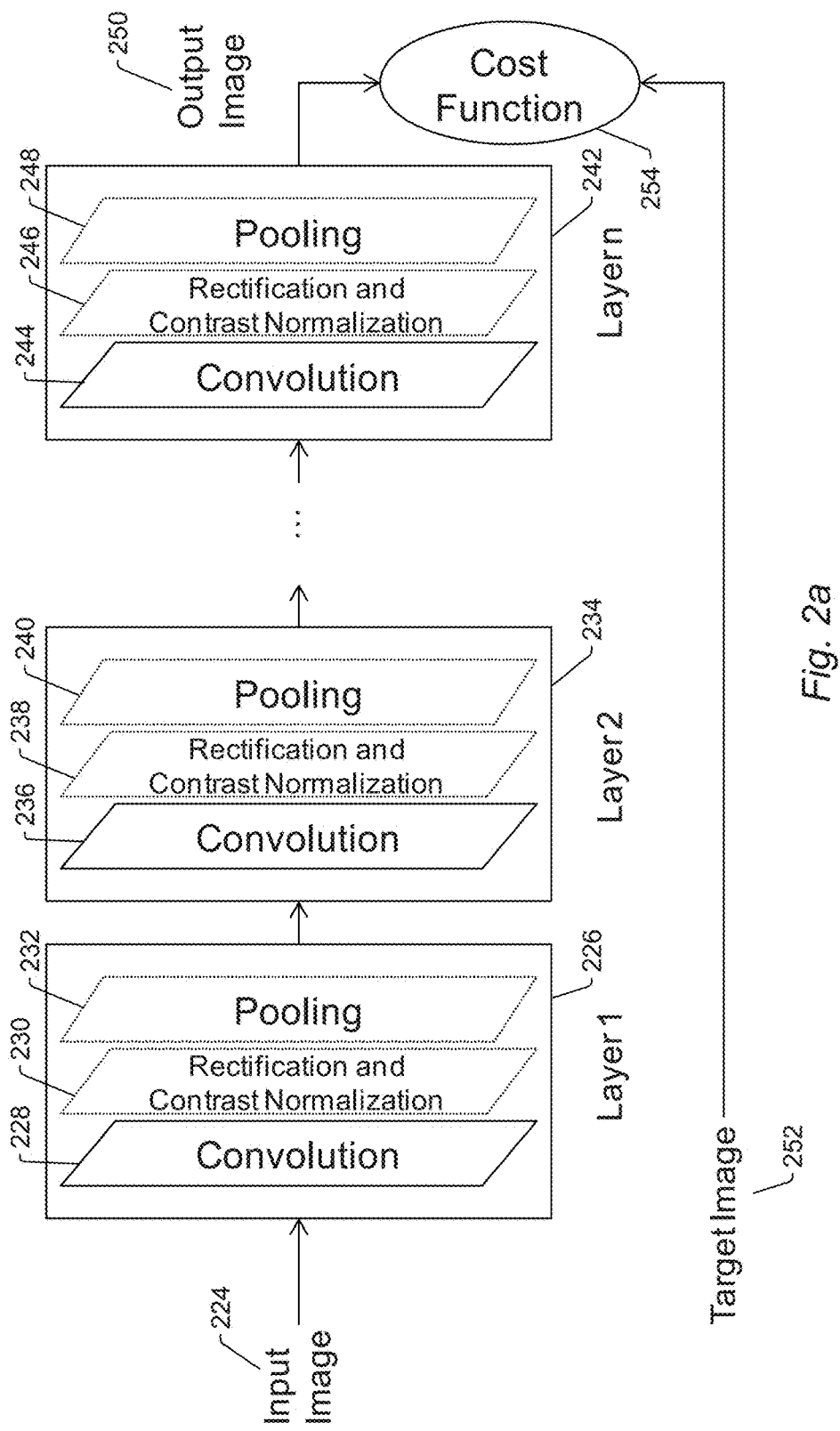
FIGS. 2a-2b are schematic diagrams illustrating various embodiments of a generative model that may be included in and/or used by the embodiments described herein.

In one embodiment, the generative model is configured as a convolutional neural network (CNN). In this manner, a CNN may be used as a DL engine. One embodiment of a CNN configuration that may be used in the embodiments described herein is shown in FIG. 2a. As shown in this figure, input image 224 may be input to first layer 226 of the CNN, layer 1. Layer 1 may include various kernels such as convolution kernel 228, rectification and contrast normalization kernel 230, and pooling kernel 232 as shown in layer 1. The output of layer 1 may be input to second layer 234 of the CNN, layer 2. This layer may also include convolution kernel 236, rectification and contrast normalization kernel 238, and pooling kernel 240. The output of this layer may be input to one or more additional layers (shown schematically in the figure by the ellipsis) until the input of the next to the last layer (not shown in FIG. 2a) is input to final layer 242 of the CNN, layer n. Final layer 242 may include convolution kernel 244, rectification and contrast normalization kernel 246, and pooling kernel 248. The output of this final layer may be output image 250 that may be compared to target image 252, which may be an optical image acquired by the optical inspection subsystem by imaging an actual wafer.

Cost function 254 may be used to determine differences between the output image and the target image and to modify one or more parameters of one or more layers of the CNN based on the differences. Examples of cost functions that can be used for training of the CNN include Euclidean distance, cross-entropy, and any other suitable cost functions known in the art. A backpropagation algorithm may minimize the cost function and converge to an optimal network.

Figure 2B:
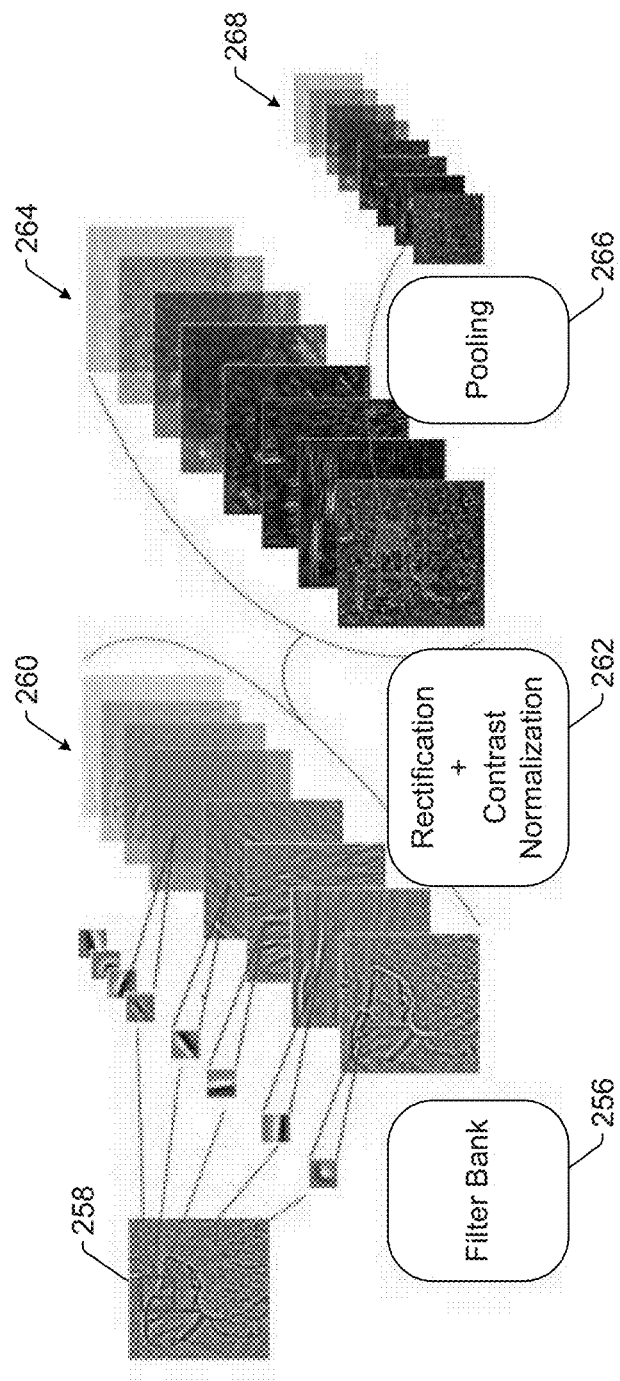

In this manner, the CNN may convert an input image to an output image. Each layer contains a convolution kernel with sets of convolution kernels operating on the input image to the layer, and the rectification/contrast normalization and pooling layers are optional. FIG. 2b shows an example of the details of each layer that may be included in a CNN used in the embodiments described herein. (FIG. 2b has been excerpted from a figure in "Tutorial on Deep Learning for Vision," CVPR 2014, which is incorporated by reference as if fully set forth herein. The generative models described herein may be further configured as described in this document.) As shown in FIG. 2b, each layer of a CNN may include filter bank 256 to which image 258 is input. Filter bank 256 performs convolution on the input image to generate set 260 of sub-images. The sub-images are input to rectification and contrast normalization kernel 262, which generates set 264 of sub-images. The sub-images generated by the rectification and contrast normalization kernel may then be input to pooling kernel 266. Output 268 of the pooling layer may then be provided to the next layer in the CNN. The kernels included in each of the layers may have any suitable configuration known in the art. In addition, the CNN may include any suitable number of layers known in the art.

In another embodiment, the generative model is configured as an auto-encoder. The auto-encoder may have any suitable configuration known in the art. In addition, the DL engine can have any applicable DL architecture and their variations or implementations.

In one embodiment, the at least one step is performed by executing the generative model and an additional generative model. For example, a DL rendering engine may be used in multiple combinations of modeling steps or in each single step with single and/or multiple DL engines. In one such embodiment, the one or more steps include a first step and a second step, and the one or more computer subsystems are configured for performing the first step by executing the generative model and performing the second step by executing the additional generative model. In this manner, different generative models may be used for different steps performed for generating the rendered image. The configurations of the different generative models will be dependent on the step(s) for which they will be used. In one such example, a different generative model may be used for each of the steps described herein that are performed to generate a rendered image. In this manner, the output of one generative model may be input to a different generative model. In some instances though, the steps described herein may be performed using a combination of one or more generative models and one or more non-generative models. In one such instance, a generative model may be used to perform one step involved in generating the rendered image while a non-generative model may be used to perform a different step involved in generating the rendered image. The non-generative model may include any suitable model that can be configured to perform one or more steps described herein, some examples of which are described further herein.

In another such embodiment, the one or more computer subsystems are configured for separately training the generative model and the additional generative model. For example, a DL rendering engine may be used in multiple combinations of modeling steps or in each single step with single and/or multiple DL engines with single or multiple trainings. As described further herein, when the generative model and/or one or more additional models are trained, rendered image(s) may be compared with optical image(s) to determine differences between those images and the differences are used to train the generative model and/or the one or more additional models. When training generative model(s), the comparisons and/or the modifications to the generative models being trained may be performed using a cost function, which may include any suitable cost function such as, but not limited to, Euclidean distance and cross entropy.

The one or more steps that may be performed by executing a generative model or more than one generative model may include any of the step(s) described herein. For example, as described further herein, the one or more steps include modeling an optical inspection image from design, which may be performed with DL using one or more of the generative models described herein. In addition, as described further herein, the one or more steps may include modeling from design (polygons) to generate optical images from an inspection tool, which may be performed with DL using one or more of the generative models described herein. As also described further herein, the one or more steps may include modeling from a stack of geometry and material information to estimate near field and/or an optical system model through a DL approach using one or more of the generative models described herein.

Figure 3:
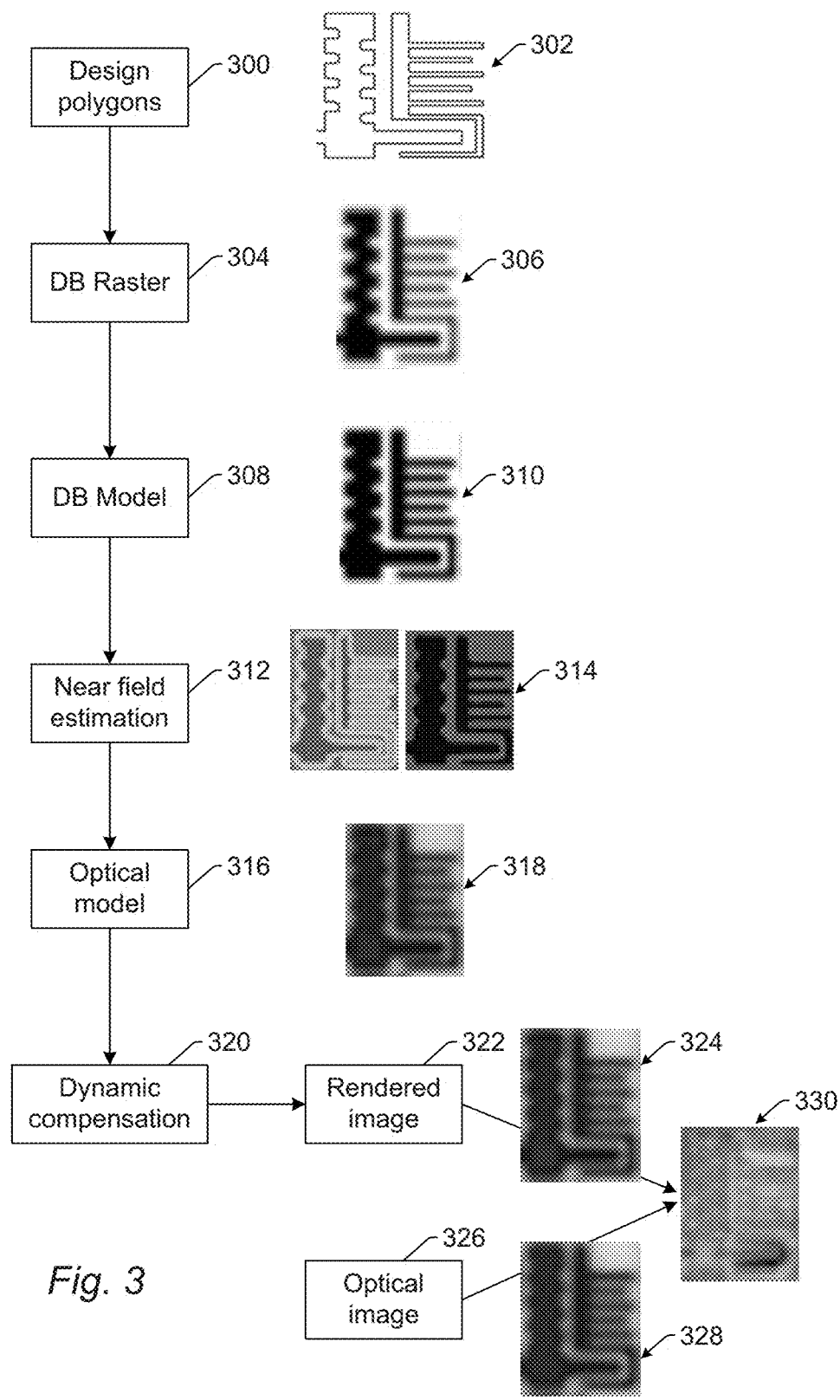
FIGS. 3-6 are flow charts illustrating various embodiments of steps that may be performed by one or more computer subsystems described herein.

In one embodiment, the one or more steps include converting polygons in the information for the design to a gray scale image. For example, as shown in FIG. 3, design polygons 300 such as design polygons 302 may be converted to gray scale image 306 by DB Raster 304. In particular, the DB Raster may convert polygons 300 to a gray scale image. DB Raster may be performed in any suitable manner. For example, the design polygons may be used to generate an intermediate binary image. Downsampling and anti-aliasing may then be performed on the intermediate binary image to generate the gray scale image.

In this manner, gray scale image 306 may be a raw gray scale image. Features in the raw gray scale image may have dimensions (e.g., CD) that are equal to the original design dimensions.

In one such embodiment, converting the polygons is performed with sub-pixel accuracy. In other words, the computer subsystem(s) may convert polygons in the design to a gray scale image with sub-pixel accuracy. Sub-pixel accuracy means that the gray scale image should be able to represent polygons with dimensions (e.g., width or height) smaller than one pixel. :For example, if there is a polygon with a height of 0.31 pixels, that height should be reflected in the gray scale image properly (as 0.31 pixels). In addition, the gray scale image should reflect the polygon position with sub-pixel accuracy. For example, if a first polygon is centered at 31.3 pixels and a second polygon is centered at 42.7 pixels, the gray scale image should be able to represent the non-integer distance between the polygons, which is 11.4 pixels (42.7 pixels−31.3 pixels). In contrast, many DB raster methods in use today can only handle polygons with sizes that are an integer of pixel number.

In another such embodiment, the one or more steps include generating a modified gray scale image by applying bias correction and corner rounding to the gray scale image. For example, as shown in FIG. 3, DB model 308 may use gray scale image 306 as input to produce modified gray scale image 310. By applying the bias correction and corner rounding to the gray scale image, the features shown in the modified gray scale image may have different dimensions and different corner rounding than the features shown in the gray scale image. For example, very often, real pattern sizes on wafers are different from the as-designed CDs due to lithography process error. Such differences are generally referred to in the art as "bias." Therefore, by modifying the gray scale image to account for such bias, the rendered images generated as described herein will simulate the optical images that would be produced by the inspection subsystem much more accurately. Appropriate bias corrections and corner rounding may be acquired from any suitable source in any suitable manner (e.g., experimentally or empirically). The bias may also be expressed in any suitable manner (e.g., as a constant for a constant bias or as a function for a nonlinear bias).

In some such embodiments, the one or more steps also include estimating a near field of the wafer based on the modified gray scale image and the information for the design printed on the wafer. For example, as shown in FIG. 3, near field estimation 312 may use modified gray scale image 310 as input to produce estimated near field 314. The information for the design used for the near field estimation may include material parameters, three dimensional (3D) effects, wavelength and angle dependency, etc. The estimated near field of the wafer is a simulation of an electromagnetic (EM) field that would be generated at or near the top surface of the wafer (i.e., at the wafer plane) by the interaction of the materials and their geometry on the wafer and the light directed to the wafer by the optical inspection subsystem. The estimated near field may include amplitude as shown in left side of estimated near field 314 and phase as shown in right side of estimated near field 314. The estimated near field may also be or include complex numbers. The estimated near field may be estimated in a number of different manners. For example, the near field may be estimated by Kirchhoff/thin mask approximation, thick mask approximation, rigorous EM simulation (e.g., finite-difference time-domain (FDTD)), rigorous EM simulation added to thin mask approximation, and any other suitable approximation, function, or model known in the art.

In one such embodiment, the one or more steps include: generating an initial rendered image that is another simulation of the image generated by the optical inspection subsystem for the design printed on the wafer based on the near field and an optical model of the optical inspection subsystem. Therefore, in the embodiments described herein, the input to optical modeling is the near field estimation and not the design database. For example, as shown in FIG. 3, optical model 316 may use estimated near field 314 as input to generate initial rendered image 318. The optical model may model with and without aberrations of the optical inspection subsystem. Generating the initial rendered image may be performed using an incoherent model, a Partial Coherence Model, the Partial Coherence-Hopkins Formulation, a linear convolution model, a linear convolution model with Hermitian quadratic form, Robust Principal Component Analysis (Robust PCA), an Abbe imaging method, a rigorous EM model, and any other suitable approximation, function, or model known in the art.

In a further embodiment, the one or more steps also include generating the rendered image from the initial rendered image by modifying the initial rendered image to minimize differences between the initial rendered image and the optical image generated by the optical inspection subsystem. For example, as shown in FIG. 3, dynamic compensation 320 performed by the computer subsystem(s) may modify initial rendered image 318 to generate rendered image 322, one example of which is shown in FIG. 3 as rendered image 324. The dynamic compensation may be performed to compensate for differences between the rendered image and an optical image such as gain and offset of the images (e.g., for tone mismatches and relatively small misalignment between the images) and differences in the images due to aberrations of the optical inspection subsystem. In addition, since the simulations described herein may intentionally be not completely rigorous, and since the materials/dimensions of features printed on the wafer may vary from design in unpredictable ways, run time compensation may be performed to reduce differences between the rendered image and the optical image. Smaller differences between the rendered image and the optical image mean that the rendered image is more similar to the optical image. In this manner, there will be significantly fewer nuisances and false defects detected by performing the dynamic compensation described herein.

In one such example, the gray scale of a rendered image may be slightly smaller than the gray scale of an optical image, and/or the rendered image may not be aligned with the optical image very well. So, simply comparing the rendered image with the optical image and detecting defects based on the comparison results may produce a significant number of nuisance defects. Therefore, the dynamic compensation described herein can be designed to reduce such systematic differences between the rendered image and the optical image. Such differences in gray scale and/or alignment can be dynamically compensated for using any suitable model, algorithm, or function known in the art. In another such example, tool aberration in the optical imaging can cause the real optical image to be different from the expected optical image. Examples of such tool aberrations include, but are not limited to, lens decentering and wafer defocus. All aberrations can cause phase errors across the exit pupil of the imaging lens (compared with the expected ideal phase distribution). By far, the most common way to describe aberrations in optical imaging systems is using Zernike polynomials. Therefore, the dynamic compensation described herein may use a description of the aberrations such as Zernike polynomials or any other suitable description of optical imaging system aberrations known in the art to modify the rendered image to thereby minimize differences between the rendered image and the optical image. Such modification may be performed using any suitable model, algorithm, or function known in the art.

As further shown in FIG. 3, optical image 326, one example of which is shown in FIG. 3 as optical image 328, may be acquired by the computer subsystem(s) from the inspection subsystem (or a computer readable storage medium in which the image was stored) and compared to rendered image 322. Such comparisons may generate difference image 330. The comparisons between the rendered image and the optical image may be performed for defect detection, which may be performed as described further herein. The comparisons between the rendered image and the optical image may also or alternatively be performed for one or more other purposes. For example, in some instances, rendered and optical images corresponding to the same (or substantially the same) portions of the design may be compared for alignment of the rendered image (and therefore the design) to the optical images. Such alignment may be performed for a number of reasons including setting up optical die-to-DB inspection as well as other reasons such as setting up or modifying one or more parameters used for dynamic compensation 320.

As described above, one or more generative models may be used to perform one or more steps performed for generating the rendered image. In one such example, one or more generative models may be used for near field estimation 312 shown in FIG. 3. In this case, one or more DL engines may learn EM fields on the surface of the wafer, which depend on material parameters, 3D effects, illumination wavelength and angle, etc. During training and rendering, the dynamic compensation is optional. In addition, during training, a cost function (not shown in FIG. 3) such as one of those described further herein may he used to compare rendered image 322 with optical image 326 and to modify one or more parameters of the DL engine(s) used for near field estimation. One or more other models may be used for all other steps shown in FIG. 3, and those one or more other models may or may not be generative models.

In another such example, one or more generative models may be used for optical model 316 shown in FIG. 3. In this case, the DL engine(s) may learn the optical model with and without aberration from the system. During training and rendering, the dynamic compensation is optional. In addition, during training, a cost function (not shown in FIG. 3) such as one of those described further herein may be used to compare rendered image 322 with optical image 326 and to modify one or more parameters of the DL engine(s) used for optical modeling. One or more other models may be used for all other steps shown in FIG. 3, and those one or more other models may or may not be generative models.

In an additional such example, one or more generative models may be used for near field estimation 312 and optical model 316 shown in FIG. 3. In this case, one or more DL engines may learn both EM fields on the surface of the wafer, which depend on material parameters, 3D effects, illumination wavelength and angle, etc., and the optical model with and without aberration from the system. In this manner, steps 312 and 316 shown in FIG. 3 may not be performed as separate steps, but may he performed as a single step whose input is modified gray scale image 310 and whose output is initial rendered image 318. During training and rendering, the dynamic compensation is optional. In addition, during training, a cost function (not shown in FIG. 3) such as one of those described further herein may be used to compare rendered image 322 with optical image 326 and to modify one or more parameters of the DL engine(s) used for near field estimation and optical modeling. One or more other models may be used for all other steps shown in FIG. 3, and those one or more other models may or may not be generative models.

In a further example, one or more generative models may be used for DB model 308 shown in FIG. 3. In this case, the DL engine(s) may learn the bias of patterns printed on the wafer from design. Application of the bias step is use case dependent in the final die-to-DB comparison. For example, detecting CD variation requires no bias correction, or bias correction to standard wafer. Particle detection preferably includes bias correction to reduce nuisance. During training and rendering, the dynamic compensation is optional. In addition, during training, a cost function (not shown in FIG. 3) such as one of those described further herein may be used to compare rendered image 322 with optical image 326 and to modify one or more parameters of the DL engine(s) used for the DB model. One or more other models may be used for all other steps shown in FIG. 3, and those one or more other models may or may not be generative models.

In yet another such example, one or more generative models may be used for DB Raster 304 and DB Model 308 shown in FIG. 3. In this case, one or more DL engines generate the rendered design including bias correction as input for EM and optical simulation (i.e., steps 312 and 316). In this manner, steps 304 and 308 shown in FIG. 3 may not be performed as separate steps, but may be performed as a single step whose input is design polygons 300 and whose output is modified gray scale image 310. During training and rendering, the dynamic compensation is optional. In addition, during training, a cost function (not shown in FIG. 3) such as one of those described further herein may be used to compare rendered image 322 with optical image 326 and to modify one or more parameters of the DL engine(s) used for DB Raster 304 and DB Model 308. One or more other models may be used for all other steps shown in FIG. 3, and those one or more other models may or may not be generative models.

In still another such example, one or more generative models may be used for DB Raster 304, DB Model 308, near field estimation 312, and optical model 316 shown in FIG. 3. In this case, one or more DL engines simulate the entire image rendering process. In this manner, steps 304, 308, 312, and 316 shown in FIG. 3 may not be performed as separate steps, but may be performed as a single step whose input is design polygons 300 and whose output is initial rendered image 318. During training and rendering, the dynamic compensation is optional. In addition, during training, a cost function (not shown in FIG. 3) such as one of those described further herein may be used to compare rendered image 322 with optical image 326 and to modify one or more parameters of the DL engine(s) used for DB Raster, DB Model, near field estimation, and optical model.

Figure 4:
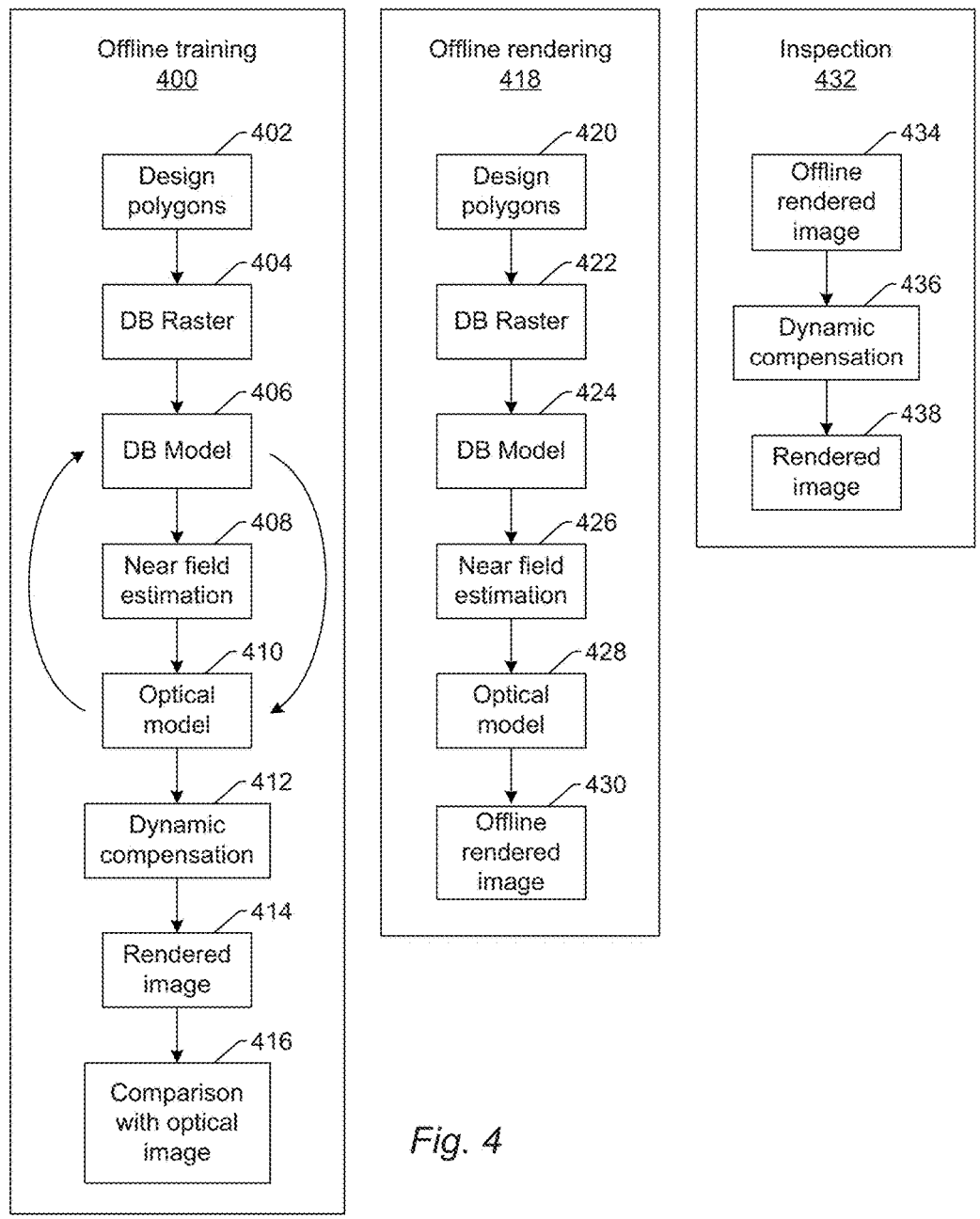

The computer subsystem(s) may perform general wafer inspection and/or post-processing with DL in three phases. For example, the computer subsystem(s) may train the DL engine(s) with images from selected samples/sites on the wafer. In one such example, the computer subsystem(s) may perform offline training 400 as shown in FIG. 4. This training may be performed for selected sites on the wafer. The computer subsystem(s) may then render images with the trained DL engine(s) from design or a is stack of design geometry and/or material for an entire die or preselected regions/locations. For example, the computer subsystem(s) may perform offline rendering 418 as shown in FIG. 4. Offline rendering may be performed for a whole die or at preselected die locations. In addition, the computer subsystem(s) may apply dynamic compensation (e.g., for gain/offset and aberration) in rendering and optical image comparison for the whole wafer (or sampled dies with predefined care areas), in real time inspection, or on output images from inspector or review tool. The computer subsystem(s) may also be configured for applying dynamic compensation (for gain/offset and aberration) in a final comparison between a rendered image and an image from an inspection and/or review tool. The computer subsystem(s) may be further configured for applying dynamic compensation (for gain/offset and aberration) in a final comparison between a rendered image and an image from the inspection and/or review tool on hot spots and/or small blocks. For example, as shown in FIG. 4, the computer subsystem(s) may perform inspection 432. Inspection may be performed online or on images output from an inspection and/or review tool. In other words, the inspection may or may not be performed online. If the inspection is performed offline, the inspection may be performed using optical images that were generated by an inspection and/or review tool and were stored in a storage medium by the inspection and/or review tool. The optical images may be acquired from the storage medium in any suitable manner.

"Offline" as that term is used herein is meant to indicate that the step(s), process(es), flow(s), etc. that are performed offline are not performed during an inspection of a wafer (e.g., not performed while the wafer is being scanned by an inspection subsystem). In contrast, "online" as that term is used herein is meant to indicate that the step(s), process(es), flow(s), etc. that are performed online are performed during an inspection of a wafer (e.g., performed while the wafer is being scanned by an inspection subsystem).

In one such example, in some embodiments, the one or more computer subsystems are configured for training the generative model and/or one or more additional models used for generating the rendered image based on: one or more additional rendered images for one or more selected sites on one or more other wafers generated by performing generating the rendered image for the one or more selected sites; and one or more optical images generated by the optical inspection subsystem for the one or more selected sites on the one or more other wafers. For example, as shown in FIG. 4, offline training 400 may use design polygons 402 as input to DB raster 404, which may be performed as described above. A gray scale image produced by DB raster 404 may be input to DB model 406, which may output a modified gray scale image as described further herein. The modified gray scale image produced by DB model 406 may be input to near field estimation 408, which may produce an estimated near field for the wafer as described further herein. The estimated near field may be input to optical model 410, which may output an initial rendered image as described further herein. The initial rendered image may be input to dynamic compensation 412, which may output rendered image 414. The computer subsystem(s) may then perform a comparison between the rendered image and an optical image, as shown in step 416.

A cost function may be used to perform the comparison of the rendered image and the optical image in step 416 and to determine errors (e.g., a sum of squared errors (SSE)) in the rendered image compared to the optical image. The cost function may be configured to use those errors to train one or more parameters of one or more of the step(s) performed by the computer subsystem(s). For example, the errors can be used to train one or more parameters of DB model 406 such as the parameters used for bias correction and/or corner rounding. In addition, the errors may be used to train one or more parameters of optical model 410. Furthermore, the arrows between the DB model and the optical model are meant to indicate that the learning that is performed based on the comparisons between the rendered image and the optical image may be a nonlinear/recursive process for the overall modeling performed by the computer subsystem(s). In addition, the errors may be used to adjust one or more parameters used for dynamic compensation (e.g., to account for day to day drifting in the parameter(s) of the optical inspection subsystem which can affect one or more characteristics of the optical image on a day to day basis).

In one such embodiment, the initial rendered image is generated for a whole die (or at preselected die locations) in the design printed on the wafer. For example, the computer subsystem(s) may perform offline rendering 418, as shown in FIG. 4. Such offline rendering may include using design polygons 420 as input to DB raster 422, which may be performed as described above. A gray scale image produced by DB raster 422 may be input to DB model 424, which may output a modified gray scale image as described further herein. DB model 424 used for offline rendering may be the DB model trained in offline training 400. The modified gray scale image produced by DB model 424 may be input to near field estimation 426, which may produce an estimated near field for the wafer as described further herein. The estimated near field may be input to optical model 428, which may output offline rendered image 430, which may be an initial rendered image as described further herein. Optical model 428 used for offline rendering may be the optical model that is trained in offline training 400.

The offline rendered image 430 for the whole die may be made up of multiple smaller rendered images that in combination span the whole die on the wafer. For example, the simulation steps described herein may be performed separately for different portions of a die, and then the results of the simulation steps may be combined in any manner to produce simulation results for a larger portion of the die (e.g., a subswath or a swath) or for the entire die. Alternatively, the simulation steps may be performed for all of the design for the whole die such that the results produced by any one simulation step are for an entire die on a wafer.

In some such embodiments, during the offline training, the cost function may be configured for training one or more parameters of one or more generative models configured to perform near field estimation 408. Such training may be performed as described further herein. In such an embodiment, during offline rendering, the one or more generative models with the trained one or more parameters may be used for near field estimation 426.

In additional such embodiments, during the offline training, the cost function may be configured for training one or more parameters of one or more generative models configured to perform optical model 410. Such training may be performed as described further herein. In such an embodiment, during offline rendering, the one or more generative models with the trained one or more parameters may be used for optical model 428.

In a further such embodiment, during the offline training, the cost function may be configured for training one or more parameters of one or more generative models configured to perform near field estimation 408 and optical model 410. Such training may be performed as described further herein.

In such an embodiment, during offline rendering, the one or more generative models with the trained one or more parameters may be used for near field estimation 426 and optical model 428.

In some such embodiments, during the offline training, the cost function may be configured for training one or more parameters of one or more generative models configured to perform DB Model 406. Such training may be performed as described further herein. In such an embodiment, during offline rendering, the one or more generative models with the trained one or more parameters may be used for DB Model 424.

In another such embodiment, during the offline training, the cost function may be configured for training one or more parameters of one or more generative models configured to perform DB Raster 404 and DB Model 406. Such training may be performed as described further herein. In such an embodiment, during offline rendering, the one or more generative models with the trained one or more parameters may be used for DB Raster 422 and DB Model 424.

In still another such embodiment, during the offline training, the cost function may be configured for training one or more parameters of one or more generative models configured to perform DB Raster 404, DB Model 406, near field estimation 408, and optical model 410. Such training may be performed as described further herein. In such an embodiment, during offline rendering, the one or more generative models with the trained one or more parameters may be used for DB Raster 422, DB Model 424, near field estimation 426, and optical model 428.

In one such embodiment, generating the rendered images includes modifying an initial rendered image to minimize differences between the initial rendered image and the optical image generated by the optical inspection subsystem, the initial rendered image is generated offline, and generating the rendered image is performed online. For example, the initial rendered image may be generated offline as shown in offline rendering 418 in FIG. 4. In addition, generating the rendered image may be performed as shown in inspection 432, which may be performed online for the whole wafer. In particular, as shown in FIG. 4, offline rendered image 434, which may be the offline rendered image generated by offline rendering 418 (i.e., offline rendered image 430), may be input to dynamic compensation 436, which may be the dynamic compensation that was trained in offline training 400, and which may be performed as described further herein. Dynamic compensation 436 may produce rendered image 438, which may be then compared to an optical image for defect detection and/or another purpose described herein. Therefore, the dynamic compensation may modify the initial rendered image that is generated offline to minimize differences between the initial rendered image and the optical image generated by the inspection subsystem thereby generating the rendered image, and the dynamic compensation may be performed online (i.e., during an inspection of the wafer).

In another such embodiment, the initial rendered image is generated for a whole die in the design printed on the wafer, and generating the rendered image is performed online for an entirety of the wafer. For example, as described above, offline rendering 418 may be performed for a whole die on the wafer while inspection 432 may be performed online for an entirety of the wafer meaning that the rendered images must be generated for an entirety of the wafer (e.g., all of the dies on the wafer).

Figure 5:
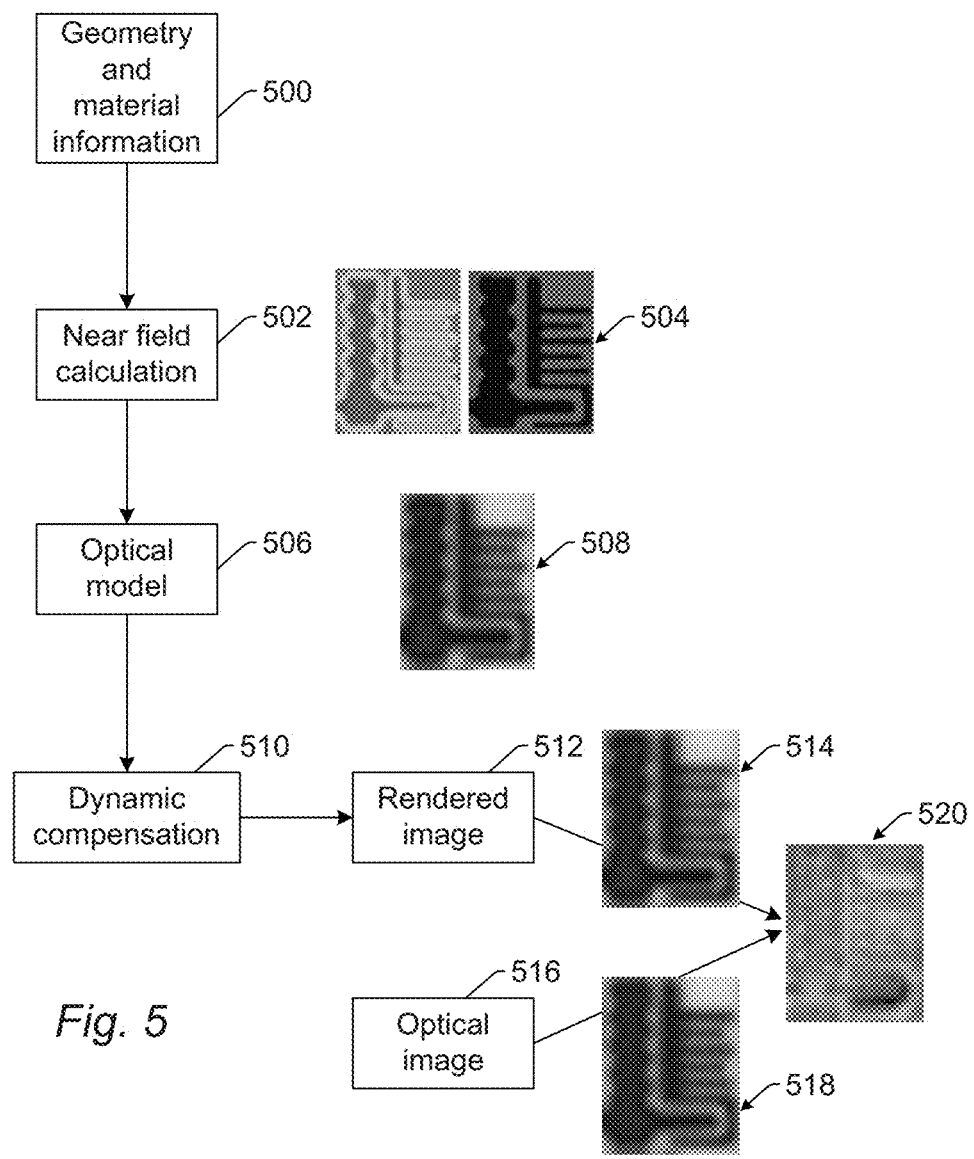

As described above, in some embodiments, the rendered image may be generated by estimating the near field of the wafer. In some instances, the near field estimation can be replaced by a near field calculation if full stack geometry and material information is available for a wafer. In one embodiment, the one or more steps include calculating a near field of the wafer based on the information for the design printed on the wafer, and the information for the design printed on the wafer includes geometry and material characteristics. For example, as shown in FIG. 5, geometry and material information 500 may be input to near field calculation 502. The geometry and material information may be a stack of geometry and material information (e.g., in a technology computer aided design (TCAD) format) for the wafer. The information for the design used for the near field calculation may also include design geometry, material parameters, wavelength and angle dependency, etc. The near field calculation may be performed in a number of ways. For example, when the 3D stack of wafer design is known in both geometry and material, the near field at the wafer plane can be calculated by solving Maxwell's equations (rigorous coupled wave analysis (RCWA) or FDTD method). The near field calculation may produce near field 504. The calculated near field of the wafer is a simulation of an EM field that would be generated at or near the top surface of the wafer (i.e., at the wafer plane) by the interaction of the materials and geometry of the wafer and the light directed to the wafer by the optical inspection subsystem. The calculated near field may include amplitude as shown in left side of calculated near field 504 and phase as shown in right side of calculated near field 504. The calculated near field may also be or include complex numbers.

In one such embodiment, the one or more steps also include generating an initial rendered image that is another simulation of the image generated by the optical inspection subsystem for the design printed on the wafer based on the near field and an optical model of the optical inspection subsystem. For example, as shown in FIG. 5, optical model 506 may use calculated near field 504 as input to generate initial rendered image 508. The optical model may model with and without aberrations of the optical inspection subsystem. The initial rendered image may be simulated based on the inspector's optical characteristics using any of the approximations, functions, or models described herein.

In a further embodiment, the one or more steps include generating the rendered image from the initial rendered image by modifying the initial rendered image to minimize differences between the initial rendered image and the optical image generated by the optical inspection subsystem. For example, as shown in FIG. 5, dynamic compensation 510 performed by the computer subsystem(s) may modify initial rendered image 508 to generate rendered image 512, one example of which is shown in FIG. 5 as rendered image 514. The dynamic compensation may be performed as described further herein.

As further shown in FIG. 5, optical image 516, one example of which is shown in FIG. 5 as optical image 518, may be acquired by the computer subsystem's) as described herein and compared to rendered image 512. Such comparisons may generate difference image 520. The comparisons between the rendered image and the optical image may be performed for defect detection, which may be performed as described further herein. The comparisons between the rendered image and the optical image may also or alternatively be performed for one or more other purposes described herein.

As described above, one or more generative models may be used to perform one or mare steps performed for generating the rendered image. In one such example, one or more generative models may be used for near field calculation 502 shown in FIG. 5. In this case, one or more DL engines may estimate EM fields on the surface of the wafer as described above. During training and rendering, the dynamic compensation is optional. In addition, during training, a cost function (not shown in FIG. 5) such as one of those described further herein may be used to compare rendered image 512 with optical image 516 and to modify one or more parameters of the DL engine(s) used for near field estimation. One or more other models may be used for all other steps shown in FIG. 5, and those one or more other models may or may not be generative models.

In another such example, one or more generative models may be used for estimating optical model 506 shown in FIG. 5. In this case, one or more DL engines may estimate the optical model of the system as described above. During training and rendering, the dynamic compensation is optional. In addition, during training, a cost function (not shown in FIG. 5) such as one of those described further herein may be used to compare rendered image 512 with optical image 516 and to modify one or more parameters of the DL engine(s) used for estimating the optical model. One or more other models may be used for all other steps shown in FIG. 5, and those one or more other models may or may not be generative models.

In an additional such example, one or more generative models may be used for near field calculation 502 and estimation of optical model 506 shown in FIG. 5. In this case, one or more DL engines simulate the entire image rendering process. In this manner, steps 502 and 506 shown in FIG. 5 may not be performed as separate steps, but may be performed as a single step whose input is geometry and material information 500 and whose output is initial rendered image 508. During training and rendering, the dynamic compensation is optional. In addition, during training, a cost function (not shown in FIG. 5) such as one of those described further herein may be used to compare rendered image 512 with optical image 516 and to modify one or more parameters of the DL engine(s) used for near field estimation and estimating the optical model.

Figure 6:
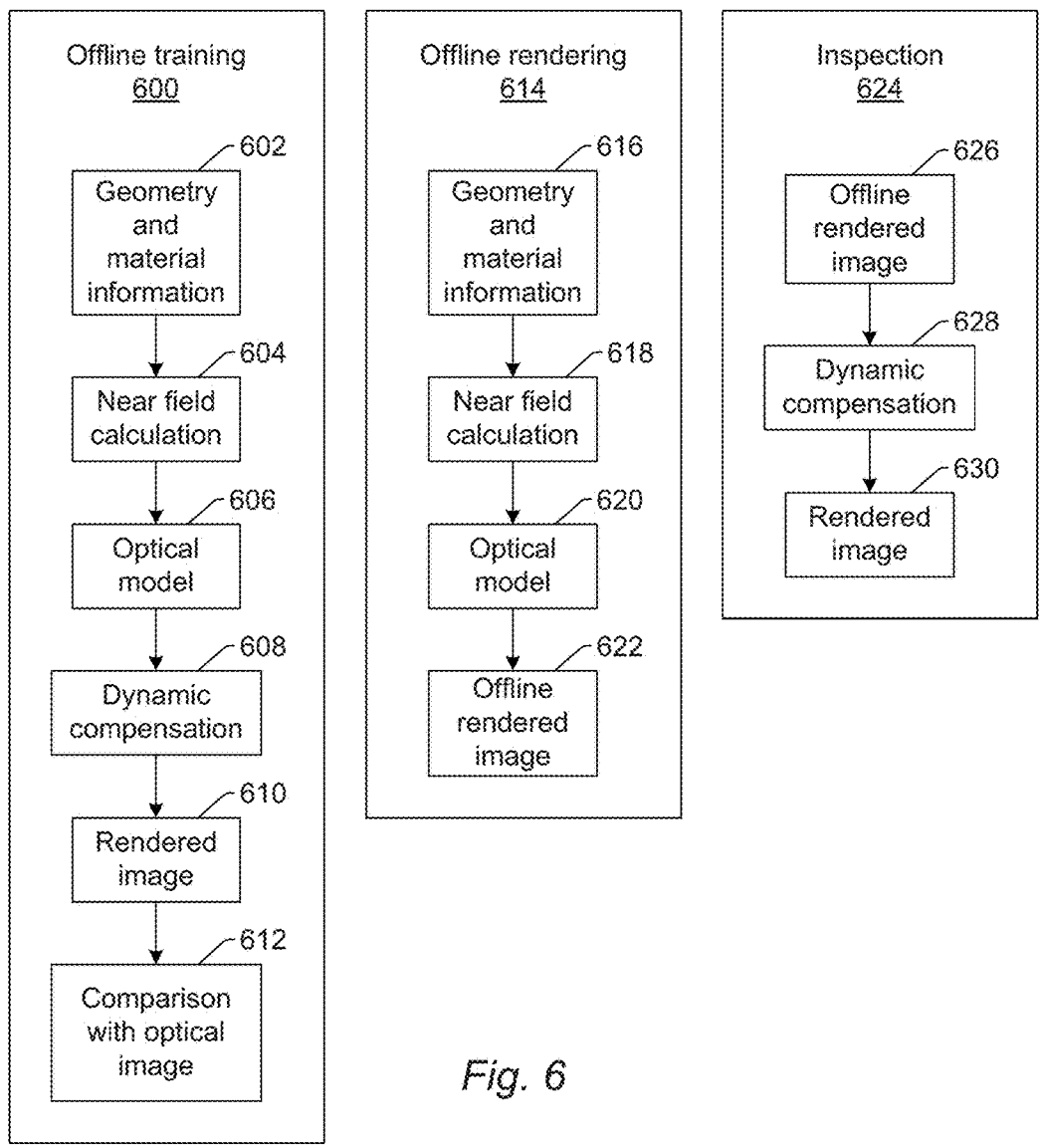

Like instances in which the computer subsystem(s) estimate the near field of the wafer, when the computer subsystem(s) calculate the near field, the computer subsystem(s) may perform general wafer inspection in three phases. For example, the computer subsystem(s) may estimate modeling parameters from selected sites. In one such example, the computer subsystem(s) may perform offline training 600 (for selected sites) as shown in FIG. 6. The computer subsystem(s) may then render images for an entire die or at preselected die locations. For example, as shown in FIG. 6, the computer subsystem(s) may perform offline rendering 614 (for a whole die on the wafer or at preselected die locations). In addition, the computer subsystem(s) may apply dynamic compensation (e.g., for gain offset and aberration) in real time inspection for the whole wafer (or sampled dies). For example, as shown in FIG. 6, the computer subsystem(s) may perform inspection 624. The inspection may be performed online or on images output from an inspection and/or review tool as described further herein. The inspection may be performed for a whole wafer, a whole die, or at preselected die locations.

In some embodiments, the one or more computer subsystems are configured for training the generative model and/or one or more additional models used for generating the rendered image based on: one or more additional rendered images for one or more selected sites on one or more other wafers generated by performing generating the rendered image for the one or more selected sites; and one or more optical images generated by the optical inspection subsystem for the one or more selected sites on the one or more other wafers. For example, as shown in FIG. 6, offline training 600 (for selected sites) may use geometry and material information 602, which may include any such information described herein, as input to near field calculation 604, which may produce a calculated near field for the wafer as described further herein. The calculated near field may be input to optical model 606, which may output an initial rendered image as described further herein. The initial rendered image may be input to dynamic compensation 608, which may output rendered image 610. The computer subsystem(s) may then perform a comparison between the rendered image and an optical image, as shown in step 612.

A cost function may be used to perform the comparison of the rendered image and the optical image in step 612 and to determine errors (e.g., a sum of squared errors (SSE)) in the rendered image compared to the optical image. The cost function may be configured to use those errors to train one or more parameters of one or more of the step(s) performed by the computer subsystem(s). For example, the cost function can be used to train one or more parameters of optical model 606. In addition, the cost function may be used to adjust one or more parameters used for dynamic compensation (e.g., to account for day to day drifting in the parameter(s) of the optical inspection subsystem which can affect one or more characteristics of the optical image on a day to day basis).

In one such embodiment, the initial rendered image is generated for a whole die in the design printed on the wafer. For example, the computer subsystem(s) may perform offline rendering (for a whole die) 614 as shown in FIG. 6. Such offline rendering may is include using geometry and material information 616, which may include any of such information described herein, as input to near field calculation 618, which may produce a calculated near field for the wafer as described further herein. The calculated near field may be input, to optical model 620, which may output offline rendered image 622, which may be an initial rendered image as described further herein. Optical model 620 used for offline rendering 614 may be the optical model that is trained in offline training 600. The offline rendered image may be otherwise generated as described further herein for the whole die.

In some such embodiments, during the offline training, the cost function may be configured for training one or more parameters of one or more generative models configured to perform near field calculation 604 (or estimation). Such training may be performed as described further herein. In such an embodiment, during offline rendering, the one or more generative models with the trained one or more parameters may be used for near field calculation 618 (or estimation).

In additional such embodiments, during the offline training, the cost function may be configured for training one or more parameters of one or more generative models configured to perform estimation of optical model 606. Such training may be performed as described further herein. In such an embodiment, during offline rendering, the one or more generative models with the trained one or more parameters may be used for optical model 620 estimation.

In another such embodiment, during the offline training, the cost function may be configured for training one or more parameters of one or more generative models configured to perform near field calculation 604 (or estimation) and estimation of optical model 606. Such training may be performed as described further herein. In such an embodiment, during offline rendering, the one or more generative models with the trained one or more parameters may be used for near field estimation 618 and estimation of optical model 620.

In one such embodiment, generating the rendered images includes modifying an initial rendered image to minimize differences between the initial rendered image and the optical image generated by the optical inspection subsystem, the initial rendered image is generated offline, and generating the rendered image is performed online. For example, the initial rendered image may be generated offline as shown in offline rendering 614 in FIG. 6. In addition, generating the rendered image may be performed as shown in inspection 624, which may be performed online for the whole wafer. In particular, as shown in FIG. 6, offline rendered image 626, which may be the offline rendered image generated by offline rendering 614 (i.e., offline rendered image 622) may be input to dynamic compensation 628, which may be the dynamic compensation that was trained in offline training 600, and which may be performed as described further herein. Dynamic compensation 628 may produce rendered image 630, which may he then compared to an optical image for defect detection and/or any other purposes described herein. Therefore, the dynamic compensation may modify the initial rendered image that is generated offline to minimize differences between the initial rendered image and the optical image generated by the inspection subsystem thereby generating the rendered image, and the dynamic compensation may be performed online (i.e., during an inspection of the wafer). In this manner, generating the rendered image may be performed online.

In another such embodiment, the initial rendered image is generated for a whole die in the design printed on the wafer, and generating the rendered image is performed online for an entirety of the wafer. For example, as described above, offline rendering 614 may be performed for a whole die on the wafer while inspection 624 may be performed online for an entirety of the wafer, meaning that the rendered images may be generated for an entirety of the wafer (e.g., all of the dies on the wafer).

In one embodiment, generating the rendered image is performed for only one or more areas in the design printed on the wafer such that generating the rendered image is not performed for an entirety of the design. The areas(s) are also referred to herein as "hot spots" or "small blocks." Areas, hot spots, and small blocks as those terms are used herein can be defined as a unit of the circuit structure that repeats many times on a die. An example size of the areas, hot spots, and small blocks is about 500 nm by about 500 nm. In this manner, the embodiments described herein may perform the steps described herein for only some portions, but not an entirety, of a die. The hot spots and/or small blocks may be identified and/or selected in any suitable manner. For example, the hot spots and/or small blocks may be care areas in the design in which inspection is to be performed. In addition, or alternatively, the hot spots and/or small blocks may be relatively small portions of the design that are repeated two or more times within the design. In this manner, generating the initial rendered image may be performed for only one small block, but that same initial rendered image may be dynamically compensated (possibly in different manners) and then compared to multiple optical images generated at different instances of the same small block of the design printed on the wafer. Generating the rendered image for only one or more areas may otherwise be performed as described herein (e.g., as shown in FIGS. 3 and 5).

The computer subsystem(s) may be configured for hot spot or small block wafer inspection in three phases. For example, the computer subsystem(s) may estimate modeling parameters from selected sites. In one such example, the computer subsystem(s) may perform offline training 400 shown in FIG. 4 and 600 shown in FIG. 6 in which the selected sites are replaced with selected hot spot and/or small block sites. The computer subsystem(s) may also render images for all hot spots/small blocks for one die. For example, the computer subsystem(s) may perform offline rendering 418 as shown in FIG. 4 and 614 as shown in FIG. 6, but instead of performing the offline rendering for the whole die, the offline rendering is performed for all hot spots and/or small blocks in one die. In addition, the computer subsystem(s) may apply dynamic compensation for gain/offset and aberration) in real time or offline inspection of all hot spots/small blocks in a whole wafer (or sampled dies). For example, the computer subsystem(s) may be configured for performing inspection 432 as shown in FIG. 4 and 624 as shown in FIG. 6 except that instead of the inspection being performed for the whole wafer, the inspection is performed for only hot spots and/or small blocks on the whole wafer.

In an embodiment, the computer subsystem(s) are configured for training the generative model and/or one or more additional models used for generating the rendered image based on: two or more additional rendered images for two or more areas on one or more other wafers generated by performing generating the rendered image for the two or more areas; and two or more optical images generated by the optical inspection subsystem for the two or more areas on the one or more other wafers. These steps may be performed as described herein (as shown in offline training 400 shown in FIG. 4 and offline training 600 shown in FIG. 6), where the selected sites are the two or more areas (e.g., two or more hot spots and/or small blocks).

The training performed for a first of the two or more areas is performed differently than the training performed for a second of the two or more areas. In this manner, if the interesting area for inspection or post-processing is for hot spots, or small blocks (having an example size of about 300 nm×about 300 nm) that repeat many times within a die, the DL engine(s) and the other models) described herein may be customized for each hot spot/small block type or groups of types. For example, if a first hot spot includes a first portion of the design having first characteristics (e.g., dense lines) and a second hot spot includes a second portion of the design having second characteristics (e.g., sparse contact holes) that are different from the first characteristics, the first and second hot spots may be printed on the wafer differently (e.g., with different bias and corner rounding) and may be imaged by the optical inspection subsystem differently (e.g., with different resolution, contrast, etc.). Therefore, one or more models (e.g., the DB model and/or the optical model) used for generating rendered images for the different hot spots would preferably be customized to account for such differences in the processes involved in generating actual optical images of the different hot spots. Therefore, the offline training may generate hot spot (or small block) specific model(s) based on rendered image(s) and optical image(s) that correspond to the hot spot (or small Hock) for which the model(s) are being trained. Such training may otherwise be performed as described herein.

In one such embodiment, generating the rendered image includes modifying an initial rendered image to minimize differences between the initial rendered image and the optical image generated by the optical inspection subsystem, the initial rendered image is generated offline, and generating the rendered image is performed online. These steps may be performed as described further herein and shown in FIGS. 4 and 6. For example, the offline rendering shown in FIGS. 4 and 6 may be performed for hot spots and/or small blocks on one die or preselected locations, and the inspection shown in FIGS. 4 and 6 may be performed for hot spots and/or small blocks or on images output from an inspection and/or review tool.

In another such embodiment, the initial rendered image is generated for all of the two or more areas in a die in the design printed on the wafer, and generating the rendered image is further performed online for all of the two or more areas in an entirety of the wafer. For example, as described above, the offline rendering of the initial rendered image may be performed for all hot spots and/or small blocks on one die. In addition, as described further herein, the online inspection may be performed for all hot spots and/or small blocks on a whole wafer.

The infrastructure for software and hardware that performs the preparation, setup and inspection (or final comparison) described herein may be configured in a variety of different ways. For example, in one embodiment, the one or more computer subsystems include two or more computer subsystems, and at least one of the two or more computer subsystems is not part of a tool that includes the optical inspection subsystem. In this manner, the computer subsystem(s) may include at least one computer subsystem that is not part of the optical inspection tool (e.g., computer subsystem 102 shown in FIG. 1) and at least one computer subsystem that is part of the optical inspection tool (e.g., computer subsystem 36 shown in FIG. 1). Such a configuration may be advantageous when it is more suitable to perform some of the step(s) described herein offline (e.g., using computer subsystem 102) While other steps are more suitably performed online (e.g., using computer subsystem 36).

In a further embodiment, the one or more computer subsystems include at least one virtual inspection system also commonly referred to as a virtual inspector (VI). A VI can be generally defined as a computer system that can store massive amounts of output generated for a wafer by an inspection subsystem such that the output can be "played back" in a manner that mimics real time acquisition of the output during which a virtual inspection can be performed for the wafer using only the stored output. Examples of such virtual inspectors are illustrated in U.S. Pat. No. 8,126,255 issued on Feb. 28, 2012 to Bhaskar et al. and U.S. Pat. No. 9,222,895 issued on Dec. 29, 2015 to Duffy et al., which are incorporated by reference as if fully set forth herein. The computer subsystem(s) described herein may be further configured as described in these patents.

In the embodiments described herein, a VI may be particularly useful for performing one or more offline steps during setup and/or for storage of the various information and/or images generated and/or used in the embodiments described herein. For example, a VI may be particularly useful for setup of the die-to-DB inspection described herein. In one such example, a VI may be configured for extracting design clips (i.e., relatively small portions of an entire design of a die on a wafer) from a design DB or file. In addition, a VI may be configured for generating the initial rendered images described herein and storing the initial rendered images. In addition, since the VI may be capable of storing massive amounts of images generated for physical wafers (i.e., actual wafers), the VI may be particularly suitable for tuning one or more parameters of the generative model(s) and/or one or more of the additional models described herein using both simulated images and actual wafer images.

A VI may also be configured for performing one or more of the steps described herein online. For example, a VI may be configured to perform the die-to-DB inspection (i.e., the image compare and defect detection steps described herein) online (and offline as well). Furthermore, since a VI may include multiple image computer nodes, performance of any of the steps described herein can be distributed across the multiple image computer nodes thereby providing advantages for throughput. Furthermore, the rendered images may be stored on the VI and then transferred to one or more other computer subsystems (e.g., a computer subsystem that is part of an optical inspection tool) as those other computer subsystem(s) need the rendered images (e.g., for online optical die-to-DB inspection).

The computer subsystem(s) may include a prep station for training and a processing unit for rendering. The prep station and the processing unit can be the same physical unit or separate units. The computer subsystem(s) may also include a prep station for design clips and image rendering preparation, with single or multiple cores of CPU/GPU/FPGA cluster and storage. For an inspection use case, the processing unit may be the inspection tool (e.g., a combination of an optical inspection subsystem and at least one computer subsystem coupled to the optical inspection subsystem). For the post processing use case, the processing unit can be single or multiple cores of CPU/GPU/FPGA cluster and storage, which may be the same or different than the prep station. In addition, the computer subsystems may be coupled by a network between the prep station and processing unit (e.g., a computer subsystem of the inspection tool) to transfer rendered images. The computer subsystem(s) may also include a design/TCAD based offline image rendering engine on the prep station or the inspection tool/processing unit. The computer subsystem(s) may further include a design/TCAD based offline training engine on the prep station or the inspection tool/processing unit. The prep station, processing unit, and/or inspection tool hardware can be optimized to speed up the DL engine(s).

In some such embodiments, the infrastructure used for preparing the design DB may include a DB in which design information is stored (e.g., one or more reticle design files (RDFS)) and a server coupled to the DB and image computer(s) and/or VI(s). The server and-/or the image computer(s) and/or VI(s) may extract design clips from the DB thereby preparing the design DB for use by the embodiments described herein. The image computer(s) and/or the VI(s) may store the extracted design clips in a design clip DB, which may have any suitable format known in the art.

The infrastructure used for design rendering may include the image computer(s) and/or VI(s) of the infrastructure configured for preparing the design data. The image computer(s) and/or VI(s) may be configured to render the design (e.g., from the design clips stored in the design clip DB) to generate the rendered images described herein. In addition, the image computer(s) and/or the VI(s) may store the rendered images in a rendered image DB, which may have any suitable format known in the art.

The infrastructure configured for performing the die-to-DB inspection may include image computer(s), which may be different from the image computer(s) included in the infrastructure configured for preparing the design DB and the image computer(s) included in the infrastructure configured for design rendering. The image computer(s) included in the infrastructure for performing the die-to-DB inspection may be configured to acquire the rendered images from the rendered image DB. These image computer(s) may also acquire the optical images generated by the optical inspection subsystem and perform one or more steps using the rendered and optical images such as pixel-to-design alignment (PDA) and defect detection. In this manner, the image computer(s) may perform inspection with a rendered die image.

The infrastructure configured for the inspection may also include one or more user interfaces (UIs) coupled to the image computer(s) such that the results produced by the image computer(s) can be provided to a user through the one or more UIs and/or such that input and/or instructions can be received from the user through the one or more The UI(s) may include any suitable tills known in the art (e.g., such as a UI that is used by commercially available inspection tools and configured to have the capability described herein).

Each of the embodiments of the system described herein may be further configured according to any other embodiment(s) described herein. Each of the embodiments described herein may also be further configured as described in U.S. patent application Ser. No. 15/088,081 by Wells et al. filed Mar. 31, 2016, Ser. No. 15/176,139 by Zhang et al. filed Jun. 7, 2016, and Ser. No. 15/353,210 by Bhaskar et al. filed Nov. 16, 2016, which are incorporated by reference as if fully set forth herein.

Another embodiment relates to a computer-implemented method for detecting defects on a wafer. The method includes steps for each of the functions of the computer subsystem(s) described above. The optical inspection subsystem is configured as described herein.

Each of the steps of the method may be performed as described further herein. The method may also include any other step(s) that can be performed by the inspection subsystem and or computer subsystem(s) or system(s) described herein. The steps of the method are performed by one or more computer systems, which may be configured according to any of the embodiments described herein. In addition, the method described above may be performed by any of the system embodiments described herein.

Figure 7:
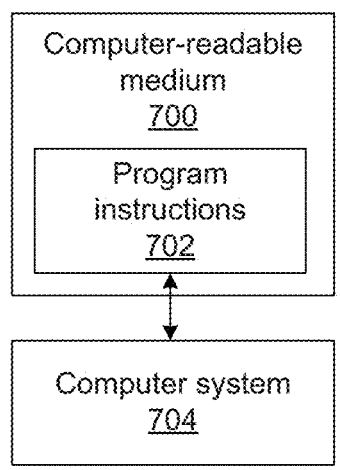
FIG. 7 is a block diagram illustrating one embodiment of a non-transitory computer-readable medium storing program instructions executable on a computer system for performing one or more of the computer-implemented methods described herein.

An additional embodiment relates to a non-transitory computer-readable medium storing program instructions executable on a computer system for performing a computer-implemented method for detecting defects on a wafer. One such embodiment is shown in FIG. 7. In particular, as shown in FIG. 7, non-transitory computer-readable medium 700 includes program instructions 702 executable on computer system 704. The computer-implemented method may include any step(s) of any method(s) described herein.

Program instructions 702 implementing methods such as those described herein may be stored on computer-readable medium 700. The computer-readable medium may be a storage medium such as a magnetic or optical disk, a magnetic tape, or any other suitable non-transitory computer-readable medium known in the art.

The program instructions may be implemented in any of various ways, including procedure-based techniques, component-based techniques, and/or object-oriented techniques, among others. For example, the program instructions may be implemented using ActiveX controls, C++ objects, JavaBeans, Microsoft Foundation Classes ("MFC"), SSE (Streaming SIMD Extension) or other technologies or methodologies, as desired.

Computer system 704 may be configured according to any of the embodiments described herein.

All of the methods described herein may include storing results of one or more steps of the method embodiments in a computer-readable storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc.

Further modifications and alternative embodiments of various aspects of the invention will be apparent to those skilled in the art in view of this description. For example, methods and systems for detecting defects on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system configured to detect defects on a wafer, comprising:
an optical inspection subsystem comprising at least a light source and a detector, wherein the light source is configured to generate light that is directed to a wafer, and wherein the detector is configured to detect light from the wafer and to generate images responsive to the detected light; and
one or more computer subsystems configured for:
generating a rendered image based on information for a design printed on the wafer, wherein the rendered image is a simulation of an image generated by the optical inspection subsystem for the design printed on the wafer, wherein generating the rendered image comprises one or more steps, and wherein the one or more computer subsystems are further configured for performing at least one of the one or more steps by executing a generative model;
comparing the rendered image to an optical image of the wafer generated by the optical inspection subsystem, wherein the design is printed on the wafer using a reticle; and
detecting defects on the wafer based on results of the comparing.

2. The system of claim 1, wherein the at least one step is further performed by executing the generative model and an additional generative model.

3. The system of claim 2, wherein the one or more steps comprise a first step and a second step, and Wherein the one or more computer subsystems are further configured for performing the first step by executing the generative model and performing the second step by executing the additional generative model.

4. The system of claim 2, wherein the one or more computer subsystems are further configured for separately training the generative model and the additional generative model.

5. The system of claim 1, wherein the generative model is configured as a convolutional neural network.

6. The system of claim 1, wherein the generative model is configured as an auto-encoder.

7. The system of claim 1, wherein the one or more steps comprise converting polygons in the information for the design to a gray scale image.

8. The system of claim 7, wherein said converting the polygons is performed with sub-pixel accuracy.

9. The system of claim 7, wherein the one or more steps further comprise generating a modified gray scale image by applying bias correction and corner rounding to the gray scale image.

10. The system of claim 9, wherein the one or more steps further comprise estimating a near field of the wafer based on the modified gray scale image and the information for the design printed on the wafer.

11. The system of claim 10, wherein the one or more steps further comprise generating an initial rendered image that is another simulation of the image generated by the optical inspection subsystem for the design printed on the wafer based on the near field and an optical model of the optical inspection subsystem.

12. The system of claim 11, wherein the one or more steps further comprise generating the rendered image from the initial rendered image by modifying the initial rendered image to minimize differences between the initial rendered image and the optical image generated by the optical inspection subsystem.

13. The system of claim 1, wherein the one or more steps comprise calculating a near field of the wafer based on the information for the design printed on the wafer, and wherein the information for the design printed on the wafer comprises geometry and material characteristics.

14. The system of claim 13, wherein the one or more steps further comprise generating an initial rendered image that is another simulation of the image generated by the optical inspection subsystem for the design printed on the wafer based on the near field and an optical model of the optical inspection subsystem.

15. The system of claim 14, wherein the one or more steps further comprise generating the rendered image from the initial rendered image by modifying the initial rendered image to minimize differences between the initial rendered image and the optical image generated by the optical inspection subsystem.

16. The system of claim 1, wherein the one or more computer subsystems are further configured for training the generative model based on: one or more additional rendered images for one or more selected sites on one or more other wafers generated by performing said generating for the one or more selected sites; and one or more optical images generated by the optical inspection subsystem for the one or more selected sites on the one or more other wafers.

17. The system of claim 16, wherein generating the rendered image further comprises modifying an initial rendered image to minimize differences between the initial rendered image and the optical image generated by the optical inspection subsystem, wherein the initial rendered image is generated offline, and wherein generating the rendered image is performed online.

18. The system of claim 17, wherein the initial rendered image is generated for a whole die in the design printed on the wafer, and wherein generating the rendered image is further performed online for an entirety of the wafer.

19. The system of claim 1, wherein the one or more computer subsystems are further configured for training one or more additional models used for said generating based on: one or more additional rendered images for one or more selected sites on one or more other wafers generated by performing said generating for the one or more selected sites; and one or more optical images generated by the optical inspection subsystem for the one or more selected sites on the one or more other wafers.

20. The system of claim 19, wherein generating the rendered image further comprises modifying an initial rendered image to minimize differences between the initial rendered image and the optical image generated by the optical inspection subsystem, wherein the initial rendered image is generated offline, and wherein generating the rendered image is performed online.

21. The system of claim 20, wherein the initial rendered image is generated for a whole die in the design printed on the wafer, and wherein generating the rendered image is further performed online for an entirety of the wafer.

22. The system of claim 1, wherein said generating is performed for only one or more areas in the design printed on the wafer such that said generating is not performed for an entirety of the design.

23. The system of claim 1, wherein the one or more computer subsystems are further configured for training the generative model based on: two or more additional rendered images for two or more areas on one or more other wafers generated by performing said generating for the two or more areas; and two or more optical images generated by the optical inspection subsystem for the two or more areas on the one or more other wafers, and wherein said training performed for a first of the two or more areas is performed differently than said training performed for a second of the two or more areas.

24. The system of claim 23, wherein generating the rendered image further comprises modifying an initial rendered image to minimize differences between the initial rendered image and the optical image generated by the optical inspection subsystem, wherein the initial rendered image is generated offline, and wherein generating the rendered image is performed online.

25. The system of claim 24, wherein the initial rendered image is generated for all of the two or more areas in a die in the design printed on the wafer, and wherein generating the rendered image is further performed online for all of the two or more areas in an entirety of the wafer.

26. The system of claim 1, wherein the one or more computer subsystems are further configured for training one or more additional models used for said generating based on: two or more additional rendered images for two or more areas on one or more other wafers generated by performing said generating for the two or more areas; and two or more optical images generated by the optical inspection subsystem for the two or more areas on the one or more other wafers, and wherein said training performed for a first of the two or more areas is performed differently than said training performed for a second of the two or more areas.

27. The system of claim 26, wherein generating the rendered image further comprises modifying an initial rendered image to minimize differences between the initial rendered image and the optical image generated by the optical inspection subsystem, wherein the initial rendered image is generated offline, and wherein generating the rendered image is performed online.

28. The system of claim 27, wherein the initial rendered image is generated for all of the two or more areas in a die in the design printed on the wafer, and wherein generating the rendered image is further performed online for all of the two or more areas in an entirety of the wafer.

29. The system of claim 1, wherein the one or more computer subsystems comprise two or more computer subsystems, and wherein at least one of the two or more computer subsystems is not part of a tool that includes the optical inspection subsystem.

30. The system of claim 1, wherein the one or more computer subsystems comprise at least one virtual inspection system.

31. The system of claim 1, wherein the one or more computer subsystems are further configured for determining if the reticle passes qualification based on the detected defects.

32. The system of claim 1, wherein the one or more computer subsystems are further configured for determining a performance of one or more process steps performed on the wafer based on the detected defects.

33. The system of claim 32, wherein the wafer is a short loop wafer.

34. A non-transitory computer-readable medium, storing program instructions executable on a computer system for performing a computer-implemented method for detecting defects on a wafer, wherein the computer-implemented method comprises:

generating a rendered image based on information for a design printed on a wafer, wherein the rendered image is a simulation of an image generated by an optical inspection subsystem for the design printed on the wafer, wherein the optical inspection subsystem comprises at least a light source and a detector, wherein the light source is configured to generate light that is directed to the wafer, wherein the detector is configured to detect light from the wafer and to generate images responsive to the detected light, wherein generating the rendered image comprises one or more steps, and wherein at least one of the one or more steps is performed by executing a generative model;

comparing the rendered image to an optical image of the wafer generated by the optical inspection subsystem, wherein the design is printed on the wafer using a reticle; and detecting defects on the wafer based on results of the comparing, wherein said generating, said comparing, and said detecting are performed by one or more computer subsystems.

35. A computer-implemented method for detecting defects on a wafer, comprising:

generating a rendered image based on information for a design printed on a wafer, wherein the rendered image is a simulation of an image generated by an optical inspection subsystem for the design printed on the wafer, wherein the optical inspection subsystem comprises at least a light source and a detector, wherein the light source is configured to generate light that is directed to the wafer, wherein the detector is configured to detect light from the wafer and to generate images responsive to the detected light, wherein generating the rendered image comprises one or more steps, and wherein at least one of the one or more steps is performed by executing a generative model;

comparing the rendered image to an optical image of the wafer generated by the optical inspection subsystem, wherein the design is printed on the wafer using a reticle; and detecting defects on the wafer based on results of the comparing, wherein said generating, said comparing, and said detecting are performed by one or more computer subsystems.

* * * * *